US008939935B2

(12) United States Patent
O'Connor et al.

(10) Patent No.: US 8,939,935 B2
(45) Date of Patent: Jan. 27, 2015

(54) DRIVE MECHANISM FOR DRUG DELIVERY PUMPS WITH INTEGRATED STATUS INDICATION

(75) Inventors: Sean M. O'Connor, West Chester, PA (US); Kevin Bokelman, San Diego, CA (US); Ian B. Hanson, Wayne, PA (US); Paul F. Bente, IV, Chesterbrook, PA (US)

(73) Assignee: Unitract Syringe Pty Ltd, Sydney (AU)

( * ) Notice: Subject to any disclaimer, the term of this patent is extended or adjusted under 35 U.S.C. 154(b) by 0 days.

(21) Appl. No.: 13/600,114

(22) Filed: Aug. 30, 2012

(65) Prior Publication Data

US 2013/0060196 A1    Mar. 7, 2013

Related U.S. Application Data

(60) Provisional application No. 61/530,788, filed on Sep. 2, 2011.

(51) Int. Cl.
*A61M 5/145*    (2006.01)

(52) U.S. Cl.
CPC ....... *A61M 5/14566* (2013.01); *A61M 2205/58* (2013.01)
USPC .......................................... 604/152; 604/135

(58) Field of Classification Search
USPC ........................... 604/152, 134, 135, 131, 151
See application file for complete search history.

(56) References Cited

U.S. PATENT DOCUMENTS

| 4,004,586 A | 1/1977 | Christensen et al. |
| 4,565,543 A * | 1/1986 | Bekkering et al. ............ 604/135 |
| 4,673,400 A | 6/1987 | Martin |
| 4,685,903 A | 8/1987 | Cable et al. |
| 4,755,173 A | 7/1988 | Konopka et al. |
| 4,840,620 A | 6/1989 | Kobayashi et al. |

(Continued)

FOREIGN PATENT DOCUMENTS

| EP | 1702635 A2 | 9/2006 |
| EP | 1341569 B1 | 1/2007 |

(Continued)

OTHER PUBLICATIONS

European Patent Office, International Search Report in International Application No. PCT/US2012/053174, 4 pages (Mar. 28, 2013).

(Continued)

*Primary Examiner* — Laura Bouchelle
(74) *Attorney, Agent, or Firm* — Leydig, Voit & Mayer, Ltd.

(57) ABSTRACT

A drive mechanism having integrated status indication includes a drive housing, a status switch interconnect, a drive biasing member, a piston, and a drug container having a cap, a pierceable seal, a barrel, and a plunger seal, wherein the drive biasing member is configured to bear upon an interface surface of the piston. Drive mechanism may include an incremental status stem having a stem interconnect, wherein the stem resides within the drive housing and the piston, and wherein the stem has an interconnect which engages one or more contacts on the piston to provide incremental feedback. A drug delivery pump with integrated status indication includes a housing and an assembly platform, upon which an activation mechanism, an insertion mechanism, a fluid pathway connection, a power and control system, and the drive mechanism having a drug container may be mounted.

20 Claims, 12 Drawing Sheets

(56) References Cited

U.S. PATENT DOCUMENTS

| | | | |
|---|---|---|---|
| 5,167,816 | A | 12/1992 | Kruger et al. |
| 5,795,339 | A | 8/1998 | Erskine |
| 5,858,001 | A | 1/1999 | Tsals et al. |
| 6,248,093 | B1 | 6/2001 | Moberg |
| 6,699,218 | B2 | 3/2004 | Flaherty et al. |
| 7,063,684 | B2 | 6/2006 | Moberg |
| 7,479,135 | B2 | 1/2009 | Richter et al. |
| 7,611,503 | B2 | 11/2009 | Spohn et al. |
| 7,803,134 | B2 | 9/2010 | Sharifi et al. |
| 7,846,132 | B2 | 12/2010 | Gravesen et al. |
| 7,905,859 | B2 | 3/2011 | Bynum et al. |
| 7,967,795 | B1 | 6/2011 | Cabiri |
| 8,029,472 | B2 | 10/2011 | Leinsing et al. |
| 8,048,031 | B2 | 11/2011 | Shaw et al. |
| 8,157,769 | B2 | 4/2012 | Cabiri |
| 8,167,844 | B2 | 5/2012 | Dillard, III |
| 8,187,232 | B2 | 5/2012 | Chong et al. |
| 2004/0092878 | A1 | 5/2004 | Flaherty |
| 2007/0010789 | A1 | 1/2007 | Peter et al. |
| 2007/0179444 | A1 | 8/2007 | Causey et al. |
| 2008/0132842 | A1 | 6/2008 | Flaherty |
| 2008/0269687 | A1 | 10/2008 | Chong et al. |
| 2009/0124979 | A1 | 5/2009 | Raymond et al. |
| 2009/0204077 | A1 | 8/2009 | Hasted et al. |
| 2011/0098652 | A1 | 4/2011 | Hasted et al. |
| 2011/0166509 | A1 | 7/2011 | Gross et al. |
| 2012/0035546 | A1 | 2/2012 | Cabiri |
| 2012/0096953 | A1* | 4/2012 | Bente et al. ............ 73/862.53 |
| 2012/0123354 | A1 | 5/2012 | Woehr |

FOREIGN PATENT DOCUMENTS

| | | |
|---|---|---|
| EP | 1427471 B1 | 2/2008 |
| EP | 1695727 B1 | 7/2008 |
| EP | 1513580 B1 | 3/2009 |
| EP | 2077128 A1 | 7/2009 |
| EP | 2379134 A1 | 10/2011 |
| EP | 2429612 A1 | 3/2012 |
| EP | 2433663 A1 | 3/2012 |
| WO | WO 99/48546 A1 | 9/1999 |
| WO | WO 03-024504 A2 | 3/2003 |
| WO | WO 03-103763 A1 | 12/2003 |
| WO | WO 2004/062714 A1 | 7/2004 |
| WO | WO 2005-037350 A2 | 4/2005 |
| WO | WO 2008/024808 A2 | 2/2008 |
| WO | WO 2010/029054 A1 | 3/2010 |
| WO | WO 2010/077807 A1 | 7/2010 |
| WO | WO 2010/084113 A1 | 7/2010 |
| WO | WO 2010/112377 A1 | 10/2010 |
| WO | WO 2010/132196 A1 | 11/2010 |
| WO | WO 2011-006652 A1 | 1/2011 |
| WO | WO 2011-090956 A2 | 7/2011 |
| WO | WO 2011/121023 A1 | 10/2011 |
| WO | WO 2012/032411 A2 | 3/2012 |
| WO | WO 2012/131044 A1 | 10/2012 |

OTHER PUBLICATIONS

European Patent Office, Written Opinion of the International Searching Authority in International Application No. PCT/US2012/053174, 6 pages (Mar. 28, 2013).

European Patent Office, International Search Report in International Patent Application No. PCT/US2012/054861, 8 pages, (Feb. 18, 2013).

Preliminary Amendment and Application Data Sheet Filed in National Phase of WO 2011/090956 A2 (U.S. Appl. No. 13/521,181) (Jul. 9, 2012).

European Patent Office, Communication Relating to the Results of the Partial International Search in International Application No. PCT/US2012/053241, 2 pages (Nov. 30, 2012).

European Patent Office, International Search Report and Written Opinion in International Patent Application No. PCT/US2013/030478, mailed Nov. 18, 2013, 11 pages.

European Patent Office, International Search Report in International Application No. PCT/US2012/053241, 6 pages (Feb. 28, 2013).

European Patent Office, Written Opinion of the International Searching Authority in International Application No. PCT/US2012/053241, 8 pages (Feb. 28, 2013).

* cited by examiner

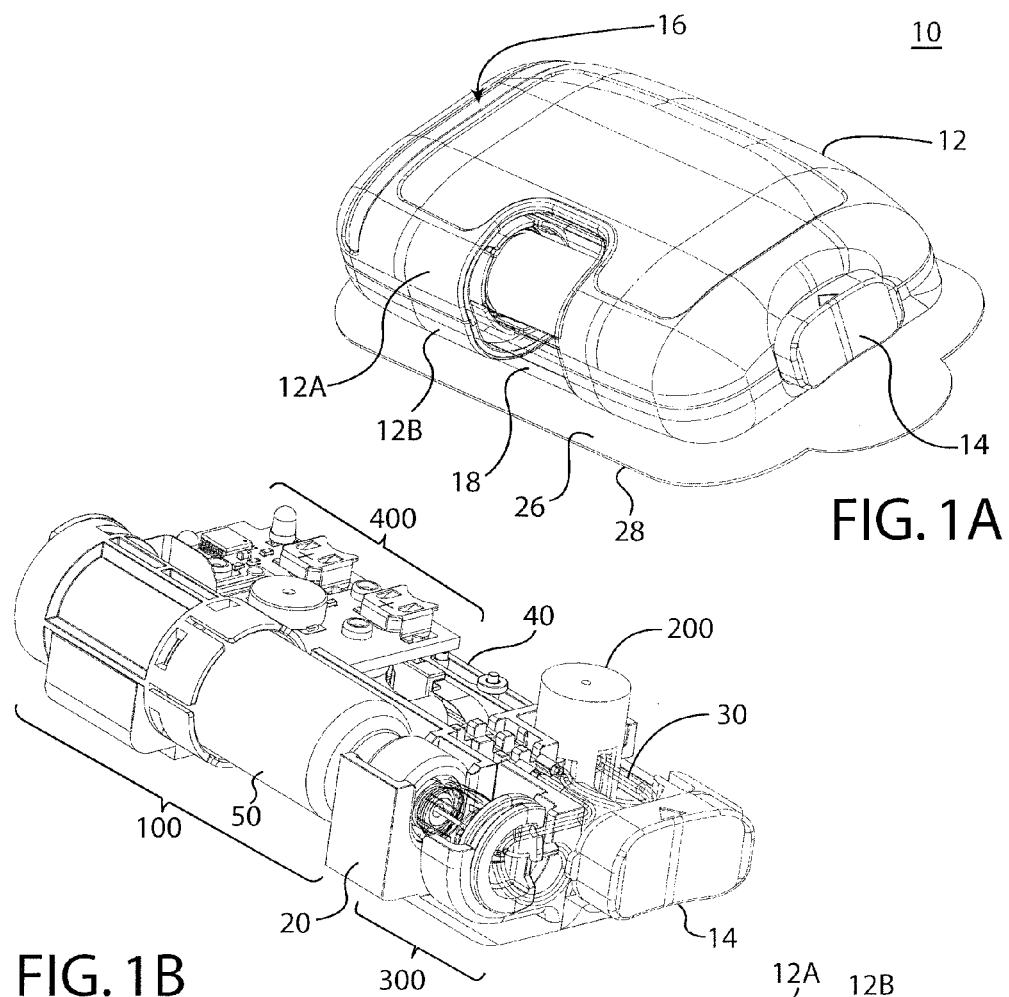
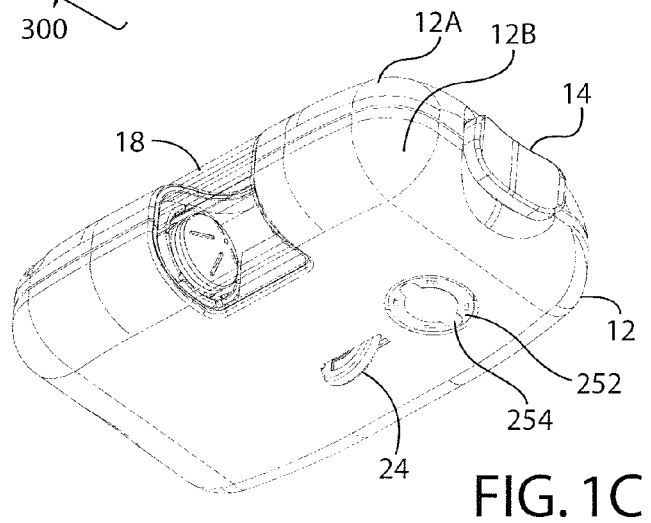
FIG. 1A
FIG. 1B
FIG. 1C

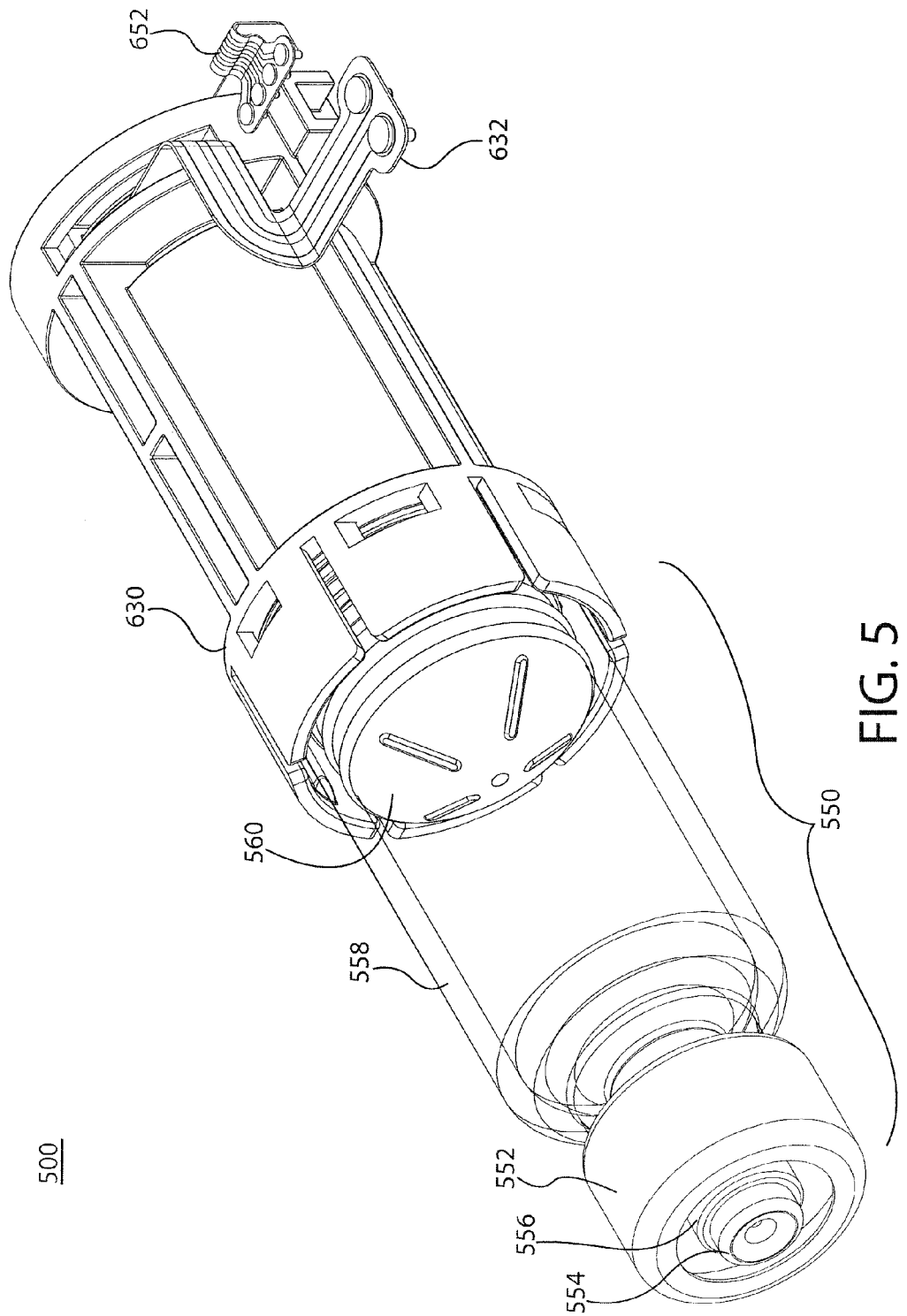

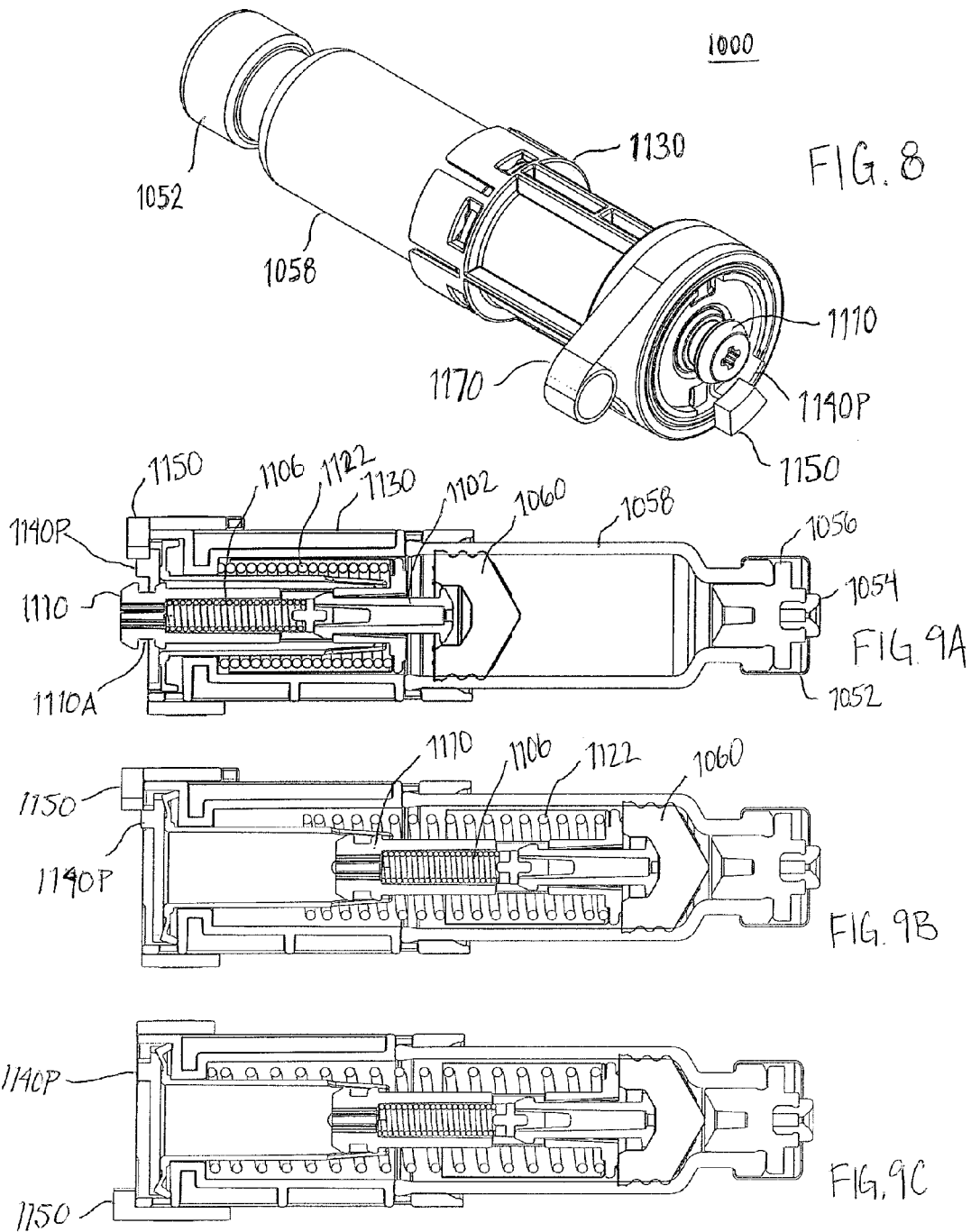

DRIVE MECHANISM FOR DRUG DELIVERY PUMPS WITH INTEGRATED STATUS INDICATION

CROSS-REFERENCE TO RELATED APPLICATIONS

This application claims priority to U.S. Provisional Application No. 61/530,788, filed on Sep. 2, 2011, which is included by reference herein in its entirety for all purposes.

FIELD

THIS INVENTION relates to drug delivery pumps. More particularly, this invention relates to drive mechanisms with integrated status indication, drug delivery pumps with status integrated drive mechanisms, the methods of operating such devices, and the methods of assembling such devices.

BACKGROUND

Parenteral delivery of various drugs, i.e., delivery by means other than through the digestive track, has become a desired method of drug delivery for a number of reasons. This form of drug delivery by injection may enhance the effect of the substance being delivered and ensure that the unaltered medicine reaches its intended site at a significant concentration. Similarly, undesired side effects associated with other routes of delivery, such as systemic toxicity, can potentially be avoided through parenteral delivery. By bypassing the digestive system of a mammalian patient, one can avoid degradation of the active ingredients caused by the catalytic enzymes in the digestive tract and liver and ensure that a necessary amount of drug, at a desired concentration, reaches the targeted site.

Traditionally, manually operated syringes and injection pens have been employed for delivering parenteral drugs to a patient. More recently, parenteral delivery of liquid medicines into the body has been accomplished by administering bolus injections using a needle and reservoir, continuously by gravity driven dispensers, or via transdermal patch technologies. Bolus injections often imperfectly match the clinical needs of the patient, and usually require larger individual doses than are desired at the specific time they are given. Continuous delivery of medicine through gravity-feed systems compromises the patient's mobility and lifestyle, and limits the therapy to simplistic flow rates and profiles. Another form of drug delivery, transdermal patches, similarly has its restrictions. Transdermal patches often require specific molecular drug structures for efficacy, and the control of the drug administration through a transdermal patch is severely limited.

Ambulatory infusion pumps have been developed for delivering liquid medicaments to a patient. These infusion devices have the ability to offer sophisticated fluid delivery profiles accomplishing bolus requirements, continuous infusion and variable flow rate delivery. These infusion capabilities usually result in better efficacy of the drug and therapy and less toxicity to the patient's system. Currently available ambulatory infusion devices are expensive, difficult to program and prepare for infusion, and tend to be bulky, heavy and very fragile. Filling these devices can be difficult and require the patient to carry both the intended medication as well as filling accessories. The devices often require specialized care, maintenance, and cleaning to assure proper functionality and safety for their intended long-term use, and are not cost-effective for patients or healthcare providers.

As compared to syringes and injection pens, pump type delivery devices can be significantly more convenient to a patient, in that doses of the drug may be calculated and delivered automatically to a patient at any time during the day or night. Furthermore, when used in conjunction with metabolic sensors or monitors, pumps may be automatically controlled to provide appropriate doses of a fluidic medium at appropriate times of need, based on sensed or monitored metabolic levels. As a result, pump type delivery devices have become an important aspect of modern medical treatments of various types of medical conditions, such as diabetes, and the like.

While pump type delivery systems have been utilized to solve a number of patient needs, manually operated syringes and injection pens often remain a preferred choice for drug delivery as they now provide integrated safety features and can easily be read to identify the status of drug delivery and the end of dose dispensing. However, manually operated syringes and injections pens are not universally applicable and are not preferred for delivery of all drugs. There remains a need for an adjustable (and/or programmable) infusion system that is precise and reliable and can offer clinicians and patients a small, low cost, light weight, simple to use alternative for parenteral delivery of liquid medicines.

SUMMARY

The present invention provides drive mechanisms with integrated status indication, drug delivery pumps which incorporate such drive mechanisms, the methods of operating such devices, and the methods of assembling such devices. The drive mechanisms of the present invention provide integrated status indication features which provide feedback to the user before, during, and after drug delivery. For example, the user may be provided an initial feedback to identify that the system is operational and ready for drug delivery. Upon activation, the system may then provide one or more drug delivery status indications to the user. At completion of drug delivery, the drive mechanism and drug pump may provide an end-of-dose indication. As the end-of-dose indication is tied to the piston reaching the end of its axial translation, the drive mechanism and drug pump provide a true end-of-dose indication to the user. Additionally, the embodiments of the present invention provide end-of-dose compliance to ensure that substantially the entire drug dose has been delivered to the user and that the status indication features have been properly contacted to provide accurate feedback to the user. Through these mechanisms, confirmation of drug dose delivery can accurately be provided to the user or administrator. Accordingly, the novel devices of the present invention alleviate one or more of the problems associated with prior art devices, such as those referred to above.

In a first embodiment, the present invention provides a drive mechanism having integrated status indication which includes: a drive housing, a status switch interconnect, a drive biasing member, a piston, and a drug container having a cap, a pierceable seal, a barrel, and a plunger seal. The drive biasing member may be configured to bear upon an interface surface of the piston. The drug container may preferably contain a drug fluid for delivery to the user. The drive mechanism may further include a connection mount attached to the pierceable seal. A cover sleeve may be utilized between the drive biasing member and the interface surface of the piston to, for example, provide more even distribution of force from the biasing member to the piston. A contact sleeve may be slidably mounted to the drive housing through an axial aperture of the drive housing, such that sleeve hooks at a distal end of the contact sleeve are caused to contact the piston between interface surface and a contact protrusion near the proximal end of the piston. The piston may also include a locking groove, between contact protrusion and the proximal end of the piston. The contact sleeve may have a radially extending ring at its proximal end, upon which reside one or more flex prongs.

The drive mechanism may further include one or more contact surfaces located on corresponding components. Such contact surfaces may be electrical contact surfaces, mechanical contact surfaces, or electro-mechanical contact surfaces. Such surfaces may initially be in contact and caused to disengage, or initially be disconnected and caused to engage, to permit a signal to be sent to and/or from the power control system. In at least one embodiment, as described further herein, the contact surfaces may be electrical contact surfaces which are initially disconnected and caused to come into engagement whereby, upon such engagement, contact surfaces are capable of continuing an energy pathway or otherwise relaying a signal to the power and control system. In another embodiment of the present invention, the contact surfaces are mechanical contact surfaces which are initially in contact and caused to disengage whereby, upon such disengagement, such disengagement is communicated to the power and control system. Such signals may be transferred across one or more interconnects to the power and control system or by mechanical action to the power and control system. Such components may be utilized within the drive mechanism to measure and relay information related to the status of operation of the drive mechanism, which may be converted by the power and control system into tactile, auditory, and/or visual feedback to the user. Regardless of the electrical or mechanical nature of the contact surfaces, the motion of the components which permits transmission of a signal to the power control system is enabled by a biasing member axially translating a contact sleeve in the distal direction during operation of the device.

The drive mechanism may include a piston extension slidably mounted at a distal end and within an axial pass-through of piston; a piston extension biasing member, which is mounted within the axial pass-through of piston and initially compressed between piston extension and piston; and, optionally, a piston biasing member support between piston extension biasing member and piston extension. The piston extension is retained within piston by interaction between one or more extension arms of the piston extension and one or more corresponding connection slots of piston. The piston extension may be utilized to perform a compliance push of drug fluid from the drug container. Additionally or alternatively, the drive mechanism may utilize a compressible plunger seal, wherein such compression capacity or distance permits a compliance push of drug fluid from the drug container. Other compliance features are described further herein.

In another embodiment of the present invention, a drive mechanism having integrated incremental status indication includes a drive housing, a drive biasing member, a piston, an incremental status stem having a stem interconnect mounted, affixed, printed, or otherwise attached thereon, and a drug container having a cap, a pierceable seal, a barrel, and a plunger seal, wherein the incremental status stem resides within axial pass-throughs of the drive housing and the piston. The incremental status stem may have one or more interconnects which contact one or more contacts on the piston to provide incremental status feedback to the user. The incremental status embodiment may similarly utilize the electrical, mechanical, or electro-mechanical interconnects and contacts, and/or one or more of the compliance features, described above.

In a further embodiment, the present invention provides a drug delivery pump with integrated status indication. The drug pump includes a housing and an assembly platform, upon which an activation mechanism, an insertion mechanism, a fluid pathway connection, a power and control system, and a drive mechanism having a drug container may be mounted. The drive biasing member may be configured to bear upon an interface surface of the piston. The drug container may preferably contain a drug fluid for delivery to the user. The drive mechanism may further include a connection mount attached to the pierceable seal. A cover sleeve may be utilized between the drive biasing member and the interface surface of the piston to, for example, provide more even distribution of force from the biasing member to the piston. A contact sleeve may be slidably mounted to the drive housing through an axial aperture of the drive housing, such that sleeve hooks at a distal end of the contact sleeve are caused to contact the piston between interface surface and a contact protrusion near the proximal end of the piston. The piston may also include a locking groove, between contact protrusion and the proximal end of the piston. The contact sleeve may have a radially extending ring at its proximal end, upon which reside one or more flex prongs. The drive mechanism may further include one or more contact surfaces located on corresponding components. Such contact surfaces may be electrical contact surfaces, mechanical contact surfaces, or electro-mechanical contact surfaces. Such surfaces may initially be in contact and caused to disengage, or initially be disconnected and caused to engage, to permit a signal to be sent to and/or from the power control system. In at least one embodiment, as described further herein, the contact surfaces may be electrical contact surfaces which are initially disconnected and caused to come into engagement whereby, upon such engagement, contact surfaces are capable of continuing an energy pathway or otherwise relaying a signal to the power and control system. In another embodiment of the present invention, the contact surfaces are mechanical contact surfaces which are initially in contact and caused to disengage whereby, upon such disengagement, such disengagement is communicated to the power and control system. Regardless of the electrical or mechanical nature of the contact surfaces, the motion of the components which permits transmission of a signal to the power control system is enabled by a biasing member axially translating a contact sleeve in the distal direction during operation of the device.

In yet another embodiment, the present invention provides a drug delivery pump with incremental status indication. The drug pump includes a housing and an assembly platform, upon which an activation mechanism, an insertion mechanism, a fluid pathway connection, a power and control system, and a drive mechanism having a drug container may be mounted, and further includes an incremental status stem having a stem interconnect mounted, affixed, printed, or otherwise attached thereon, wherein the incremental status stem resides within axial pass-throughs of the drive housing and the piston, and wherein the incremental status stem has one or more interconnects which contact one or more contacts on the piston to complete an transmission to the power and control system to provide incremental feedback to the user. The drug delivery pump with incremental status indication may similarly utilize the electrical, mechanical, or electro-mechanical interconnects and contacts, and/or one or more of the compliance features, described above.

The present invention further provides a method of assembly. The drug container may first be assembled and filled with a drug fluid. The drug container includes a cap, a pierceable seal, a barrel, and a plunger seal. The pierceable may be fixedly engaged between the cap and the barrel, at a distal end of the barrel. The barrel may be filled with a drug fluid through the open proximal end prior to insertion of the plunger seal from the proximal end of the barrel 58. An optional connection mount may be mounted to a distal end of the pierceable seal. The connection mount to guide the insertion of the piercing member of the fluid pathway connection into the barrel of the drug container. The drug container may then be mounted to a distal end of drive housing.

Prior to mounting the drug container to the housing, a switch status interconnect may be mounted to a proximal end of drive housing. A contact sleeve, having one or more sleeve hooks at a distal end and a ring at a proximal end having an electrical contact thereon, may be mounted to the drive housing through an axial pass-through from the proximal end of the drive housing. A drive biasing member may be inserted into a distal end of the drive housing. Optionally, a cover sleeve may be inserted into a distal end of the drive housing to substantially cover biasing member. A piston may be inserted into the distal end of the drive housing and through an axial pass-through of contact sleeve, such that a contact protrusion of piston is proximal to the sleeve hooks of contact sleeve. The piston and drive biasing member, and optional cover sleeve, may be compressed into the drive housing. Such assembly positions the drive biasing member in an initial compressed, energized state and preferably places a piston interface surface in contact with the proximal surface of the plunger seal within the proximal end of barrel. When a piston extension is employed, the piston extension and piston extension biasing member, and optional piston biasing member support, may be compressed into an axial pass-through of piston prior to compression of the components. Prior to, or after, installing these components into the drive mechanism housing, the primary container may be attached.

When one or more interconnects or contacts are utilized for status indication, such components may be mounted, connected, printed, or otherwise attached to their corresponding components prior to assembly of such components into the drive mechanism. When a separate incremental status stem and a corresponding stem interconnect are utilized for such incremental status indication, the stem interconnect may be mounted, affixed, printed, or otherwise attached to incremental status stem prior to assembly of the incremental status stem to the proximal end of the contact sleeve and/or the proximal end of the drive housing in a manner such that the incremental status stem resides within an axial pass-through of contact sleeve and drive housing. The incremental status stem is further mounted to reside within an axial pass-through of piston.

The novel embodiments of the present invention provide drive mechanisms with integrated status indication, which are capable of provide incremental status of the drug delivery before, during, and after operation of the device, and provides means for ensuring drug dose compliance, i.e., ensuring substantially the entire drug dose has been delivered to the user. Throughout this specification, unless otherwise indicated, "comprise," "comprises," and "comprising," or related terms such as "includes" or "consists of," are used inclusively rather than exclusively, so that a stated integer or group of integers may include one or more other non-stated integers or groups of integers. As will be described further below, the embodiments of the present invention may include one or more additional components which may be considered standard components in the industry of medical devices. The components, and the embodiments containing such components, are within the contemplation of the present invention and are to be understood as falling within the breadth and scope of the present invention.

BRIEF DESCRIPTION OF THE DRAWINGS

The following non-limiting embodiments of the invention are described herein with reference to the following drawings, wherein:

FIG. 1A shows an isometric view of a drug delivery pump having safety integrated insertion mechanisms, according to one embodiment of the present invention;

FIG. 1B shows an isometric view of the interior components of the drug delivery pump shown in FIG. 1A;

FIG. 1C shows an isometric view of the bottom of the drug delivery pump shown in FIG. 1A;

FIG. 5 shows an isometric view of a drive mechanism, according to a second embodiment of the present invention;

FIG. 8 shows an isometric view of the drive mechanism according to a further embodiment of the present invention;

FIG. 9A shows a cross-sectional view of the drive mechanism shown in FIG. 8 in an initial inactive state;

FIG. 9B shows a cross-sectional view of the drive mechanism shown in FIG. 8 in an actuated state and as the mechanism nears completion of drug delivery;

FIG. 9C shows a cross-sectional view of the drive mechanism shown in FIG. 8 as the mechanism completes drug delivery and triggers an end-of-dose signal.

DETAILED DESCRIPTION

Figure 2:
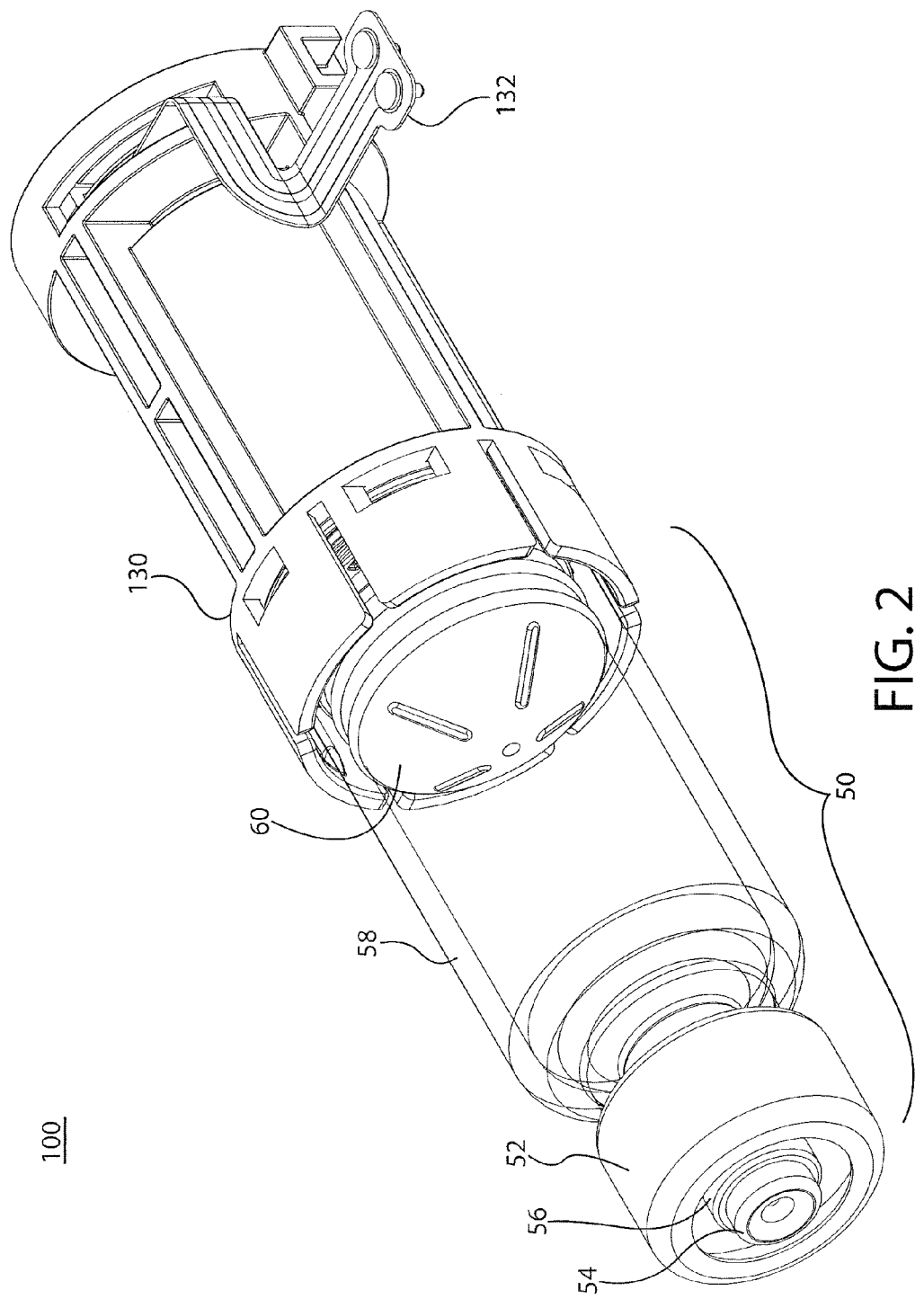
FIG. 2 shows an isometric view of a drive mechanism, according to at least one embodiment of the present invention.

As used herein to describe the drive mechanisms, drug delivery pumps, or any of the relative positions of the components of the present invention, the terms "axial" or "axially" refer generally to a longitudinal axis "A" around which the drive mechanisms are preferably positioned, although not necessarily symmetrically there-around. The term "radial" refers generally to a direction normal to axis A. The terms "proximal," "rear," "rearward," "back," or "backward" refer generally to an axial direction in the direction "P". The terms "distal," "front," "frontward," "depressed," or "forward" refer generally to an axial direction in the direction "D". As used herein, the term "glass" should be understood to include other similarly non-reactive materials suitable for use in a pharmaceutical grade application that would normally require glass, including but not limited to certain non-reactive plastics such as cyclic olefin copolymers (COC) and cyclic olefin polymers (COP). The term "plastic" may include both thermoplastic and thermosetting polymers. Thermoplastic polymers can be re-softened to their original condition by heat; thermosetting polymers cannot. As used herein, the term "plastic" refers primarily to moldable thermoplastic polymers such as, for example, polyethylene and polypropylene, or an acrylic resin, that also typically contain other ingredients such as curatives, fillers, reinforcing agents, colorants, and/or plasticizers, etc., and that can be formed or molded under heat and pressure. As used herein, the term "plastic" is not meant to include glass, non-reactive polymers, or elastomers that are approved for use in applications where they are in direct contact with therapeutic liquids that can interact with plastic or that can be degraded by substituents that could otherwise enter the liquid from plastic. The term "elastomer," "elastomeric" or "elastomeric material" refers primarily to cross-linked thermosetting rubbery polymers that are more easily deformable than plastics but that are approved for use with pharmaceutical grade fluids and are not readily susceptible to leaching or gas migration under ambient temperature and pressure. "Fluid" refers primarily to liquids, but can also include suspensions of solids dispersed in liquids, and gasses dissolved in or otherwise present together within liquids inside the fluid-containing portions of syringes. According to various aspects and embodiments described herein, reference is made to a "biasing member", such as in the context of one or more biasing members for insertion or retraction of the needle, trocar, and/or cannula. It will be appreciated that the biasing member may be any member that is capable of storing and releasing energy. Non-limiting examples include a spring, such as for example a coiled spring, a compression or extension spring, a torsional spring, and a leaf spring, a resiliently compressible or elastic band, or any other member with similar functions. In at least one embodiment of the present invention, the biasing member is a spring, preferably a compression spring.

The novel devices of the present invention provide drive mechanisms with integrated status indication and drug delivery pumps which incorporate such drive mechanisms. Such devices are safe and easy to use, and are aesthetically and ergonomically appealing for self-administering patients. The devices described herein incorporate features which make activation, operation, and lock-out of the device simple for even untrained users. The novel devices of the present invention provide these desirable features without any of the problems associated with known prior art devices. Certain non-limiting embodiments of the novel drug delivery pumps, drive mechanisms, and their respective components are described further herein with reference to the accompanying figures.

As used herein, the term "pump" is intended to include any number of drug delivery systems which are capable of dispensing a fluid to a user upon activation. Such drug delivery systems include, for example, injection systems, infusion pumps, bolus injectors, and the like. FIGS. 1A-1C show an exemplary drug delivery device according to at least one embodiment of the present invention. The drug delivery device may be utilized to administer delivery of a drug treatment into a body of a user. As shown in FIGS. 1A-1C, the drug pump 10 includes a pump housing 12. Pump housing 12 may include one or more housing subcomponents which are fixedly engageable to facilitate easier manufacturing, assembly, and operation of the drug pump. For example, drug pump 10 includes a pump housing 12 which includes an upper housing 12A and a lower housing 12B. The drug pump may further include an activation mechanism 14, a status indicator 16, and a window 18. Window 18 may be any translucent or transmissive surface through which the operation of the drug pump may be viewed. As shown in FIG. 1B, drug pump further includes assembly platform 20, sterile fluid conduit 30, drive mechanism 100 having drug container 50, insertion mechanism 200, fluid pathway connection 300, and power and control system 400. One or more of the components of such drug pumps may be modular in that they may be, for example, pre-assembled as separate components and configured into position onto the assembly platform 20 of the drug pump 10 during manufacturing.

The pump housing 12 contains all of the device components and provides a means of removably attaching the device 10 to the skin of the user. The pump housing 12 also provides protection to the interior components of the device 10 against environmental influences. The pump housing 12 is ergonomically and aesthetically designed in size, shape, and related features to facilitate easy packaging, storage, handling, and use by users who may be untrained and/or physically impaired. Furthermore, the external surface of the pump housing 12 may be utilized to provide product labeling, safety instructions, and the like. Additionally, as described above, housing 12 may include certain components, such as status indicator 16 and window 18, which may provide operation feedback to the user.

In at least one embodiment, the drug pump 10 provides an activation mechanism 14 that is displaced by the user to trigger the start command to the power and control system 400. In a preferred embodiment, the activation mechanism is a start button 14 that is located through the pump housing 12, such as through an aperture between upper housing 12A and lower housing 12B, and which contacts a control arm 40 of the power and control system 400. In at least one embodiment, the start button 14 may be a push button, and in other embodiments, may be an on/off switch, a toggle, or any similar activation feature known in the art. The pump housing 12 also provides a status indicator 16 and a window 18. In other embodiments, one or more of the activation mechanism 14, the status indicator 16, the window 18, and combinations thereof may be provided on the upper housing 12A or the lower housing 12B such as, for example, on a side visible to the user when the drug pump 10 is placed on the body of the user. Housing 12 is described in further detail hereinafter with reference to other components and embodiments of the present invention.

Drug pump is configured such that, upon activation by a user by depression of the activation mechanism, the drug pump is initiated to: insert a fluid pathway into the user; enable, connect, or open necessary connections between a drug container, a fluid pathway, and a sterile fluid conduit; and force drug fluid stored in the drug container through the fluid pathway and fluid conduit for delivery into a user. One or more optional safety mechanisms may be utilized, for example, to prevent premature activation of the drug pump. For example, an optional on-body sensor 24 (shown in FIG. 1C) may be provided in one embodiment as a safety feature to ensure that the power and control system 400, or the activation mechanism, cannot be engaged unless the drug pump 10 is in contact with the body of the user. In one such embodiment, the on-body sensor 24 is located on the bottom of lower housing 12B where it may come in contact with the user's body. Upon displacement of the on-body sensor 24, depression of the activation mechanism is permitted. Accordingly, in at least one embodiment the on-body sensor 24 is a mechanical safety mechanism, such as for example a mechanical lock out, that prevents triggering of the drug pump 10 by the activation mechanism 14. In another embodiment, the on-body sensor may be an electro-mechanical sensor such as a mechanical lock out that sends a signal to the power and control system 400 to permit activation. In still other embodiments, the on-body sensor can be electrically based such as, for example, a capacitive- or impedance-based sensor which must detect tissue before permitting activation of the power and control system 400. These concepts are not mutually exclusive and one or more combinations may be utilized within the breadth of the present invention to prevent, for example, premature activation of the drug pump. In a preferred embodiment, the drug pump 10 utilizes one or more mechanical on-body sensors. Additional integrated safety mechanisms are described herein with reference to other components of the novel drug pumps.

Power and Control System:

The power and control system 400 includes a power source, which provides the energy for various electrical components within the drug pump, one or more feedback mechanisms, a microcontroller, a circuit board, one or more conductive pads, and one or more interconnects. Other components commonly used in such electrical systems may also be included, as would be appreciated by one having ordinary skill in the art. The one or more feedback mechanisms may include, for example, audible alarms such as piezo alarms and/or light indicators such as light emitting diodes (LEDs). The microcontroller may be, for example, a microprocessor. The power and control system 400 controls several device interactions with the user and interfaces with the drive mechanism 100. In one embodiment, the power and control system 400 interfaces with the control arm 40 to identify when the on-body sensor 24 and/or the activation mechanism 14 have been activated. The power and control system 400 may also interface with the status indicator 16 of the pump housing 12, which may be a transmissive or translucent material which permits light transfer, to provide visual feedback to the user. The power and control system 400 interfaces with the drive mechanism 100 through one or more interconnects to relay status indication, such as activation, drug delivery, and end-of-dose, to the user. Such status indication may be presented to the user via auditory tones, such as through the audible alarms, and/or via visual indicators, such as through the LEDs. In a preferred embodiment, the control interfaces between the power and control system and the other components of the drug pump are not engaged or connected until activation by the user. This is a desirable safety feature that prevents accidental operation of the drug pump and may additionally maintain the energy contained in the power source during storage, transportation, and the like.

The power and control system 400 may be configured to provide a number of different status indicators to the user. For example, the power and control system 400 may be configured such that after the on-body sensor and/or trigger mechanism have been pressed, the power and control system 400 provides a ready-to-start status signal via the status indicator 16 if device start-up checks provide no errors. After providing the ready-to-start status signal and, in an embodiment with the optional on-body sensor, if the on-body sensor remains in contact with the body of the user, the power and control system 400 will power the drive mechanism 100 to begin delivery of the drug treatment through the fluid pathway connection 300 and sterile fluid conduit 30. In a preferred embodiment of the present invention, the insertion mechanism 200 and the fluid pathway connection 300 may be caused to activate directly by user operation of the activation mechanism 14. During the drug delivery process, the power and control system 400 is configured to provide a dispensing status signal via the status indicator 16. After the drug has been administered into the body of the user and after the end of any additional dwell time, to ensure that substantially the entire dose has been delivered to the user, the power and control system 400 may provide an okay-to-remove status signal via the status indicator 16. This may be independently verified by the user by viewing the drive mechanism and drug dose delivery through the window 18 of the pump housing 12. Additionally, the power and control system 400 may be configured to provide one or more alert signals via the status indicator 16, such as for example alerts indicative of fault or operation failure situations.

Other power and control system configurations may be utilized with the novel drug pumps of the present invention. For example, certain activation delays may be utilized during drug delivery. As mentioned above, one such delay optionally included within the system configuration is a dwell time which ensures that substantially the entire drug dose has been delivered before signaling completion to the user. Similarly, activation of the device may require a delayed depression (i.e., pushing) of the activation mechanism 14 of the drug pump 10 prior to drug pump activation. Additionally, the system may include a feature which permits the user to respond to the end-of-dose signals and to deactivate or power-down the drug pump. Such a feature may similarly require a delayed depression of the activation mechanism, to prevent accidental deactivation of the device. Such features provide desirable safety integration and ease-of-use parameters to the drug pumps. An additional safety feature may be integrated into the activation mechanism to prevent partial depression and, therefore, partial activation of the drug pumps. For example, the activation mechanism and/or power and control system may be configured such that the device is either completely off or completely on, to prevent partial activation. Such features are described in further detail hereinafter with regard to other aspects of the novel drug pumps.

Fluid Pathway Connection:

The fluid pathway connection 300 includes a sterile fluid conduit 30, a piercing member, a connection hub, and a sterile sleeve. The fluid pathway connection may further include one or more flow restrictors. Upon proper activation of the device 10, the fluid pathway connection 300 is enabled to connect the sterile fluid conduit 30 to the drug container of the drive mechanism 100. Such connection may be facilitated by a piercing member, such as a needle, penetrating a pierceable seal of the drug container of the drive mechanism 100. The sterility of this connection may be maintained by performing the connection within a flexible sterile sleeve. Upon substantially simultaneous activation of the insertion mechanism, the fluid pathway between drug container and insertion mechanism is complete to permit drug delivery into the body of the user.

In at least one embodiment of the present invention, the piercing member of the fluid pathway connection is caused to penetrate the pierceable seal of the drug container of the drive mechanism by direct action of the user, such as by depression of the activation mechanism by the user. For example, the activation mechanism itself may bear on the fluid pathway connection such that displacement of the activation mechanism from its original position also causes displacement of the fluid pathway connection. In a preferred embodiment, this connection is enabled by the user depressing the activation mechanism and, thereby, driving the piercing member through the pierceable seal, because this prevents fluid flow from the drug container until desired by the user. In such an embodiment, a compressible sterile sleeve may be fixedly attached between the cap of the drug container and the connection hub of the fluid pathway connection. The piercing member may reside within the sterile sleeve until a connection between the fluid connection pathway and the drug container is desired. The sterile sleeve may be sterilized to ensure the sterility of the piercing member and the fluid pathway prior to activation.

The drug pump is capable of delivering a range of drugs with different viscosities and volumes. The drug pump is capable of delivering a drug at a controlled flow rate (speed) and/or of a specified volume. In one embodiment, the drug delivery process is controlled by one or more flow restrictors within the fluid pathway connection and/or the sterile fluid conduit. In other embodiments, other flow rates may be provided by varying the geometry of the fluid flow path or delivery conduit, varying the speed at which a component of the drive mechanism advances into the drug container to dispense the drug therein, or combinations thereof. Still further details about the fluid pathway connection 300 and the sterile fluid conduit 30 are provided hereinafter in later sections in reference to other embodiments.

Insertion Mechanism:

A number of insertion mechanisms may be utilized within the drug pumps of the present invention. In at least one embodiment, the insertion mechanism 200 includes an insertion mechanism housing having one or more lockout windows, and a base for connection to the assembly platform and/or pump housing (as shown in FIG. 1B and FIG. 1C). The connection of the base to the assembly platform 20 may be, for example, such that the bottom of the base is permitted to pass-through a hole in the assembly platform to permit direct contact of the base to the body of the user. In such configurations, the bottom of the base may include a sealing membrane that is removable prior to use of the drug pump 10. The insertion mechanism may further include one or more insertion biasing members, a needle, a retraction biasing member, a cannula, and a manifold. The manifold may connect to sterile fluid conduit 30 to permit fluid flow through the manifold, cannula, and into the body of the user during drug delivery.

As used herein, "needle" is intended to refer to a variety of needles including but not limited to conventional hollow needles, such as a rigid hollow steel needles, and solid core needles more commonly referred to as a "trocars." In a preferred embodiment, the needle is a 27 gauge solid core trocar and in other embodiments, the needle may be any size needle suitable to insert the cannula for the type of drug and drug administration (e.g., subcutaneous, intramuscular, intradermal, etc.) intended. A sterile boot may be utilized within the needle insertion mechanism. The sterile boot is a collapsible sterile membrane that is in fixed engagement at a proximal end with the manifold and at a distal end with the base. In at least on embodiment, the sterile boot is maintained in fixed engagement at a distal end between base and insertion mechanism housing. Base includes a base opening through which the needle and cannula may pass-through during operation of the insertion mechanism, as will be described further below. Sterility of the cannula and needle are maintained by their initial positioning within the sterile portions of the insertion mechanism. Specifically, as described above, needle and cannula are maintained in the sterile environment of the manifold and sterile boot. The base opening of base may be closed from non-sterile environments as well, such as by for example a sealing membrane 254 (shown in FIG. 1C).

According to at least one embodiment of the present invention, the insertion mechanism is initially locked into a ready-to use-stage by lockout pin(s) which are initially positioned within lockout windows of the insertion mechanism housing. In this initial configuration, insertion biasing member and retraction biasing member are each retained in their compressed, energized states. As shown in FIG. 1B, the lockout pin(s) 208 may be directly displaced by user depression of the activation mechanism 14. As the user disengages any safety mechanisms, such as an optional on-body sensor 24 (shown in FIG. 1C), the activation mechanism 14 may be depressed to initiate the drug pump. Depression of the activation mechanism 14 may directly cause translation or displacement of control arm 40 and directly or indirectly cause displacement of lockout pin(s) 208 from their initial position within locking windows 202A of insertion mechanism housing 202. Displacement of the lockout pin(s) 208 permits insertion biasing member to decompress from its initial compressed, energized state. This decompression of the insertion biasing member drives the needle and the cannula into the body of the user. At the end of the insertion stage, the retraction biasing member is permitted to expand in the proximal direction from its initial energized state. This axial expansion in the proximal direction of the retraction biasing member retracts the needle, while maintaining the cannula in fluid communication with the body of the user. Accordingly, the insertion mechanism may be used to insert a needle and cannula into the user and, subsequently, retract the needle while retaining the cannula in position for drug delivery to the body of the user.

Figure 3:
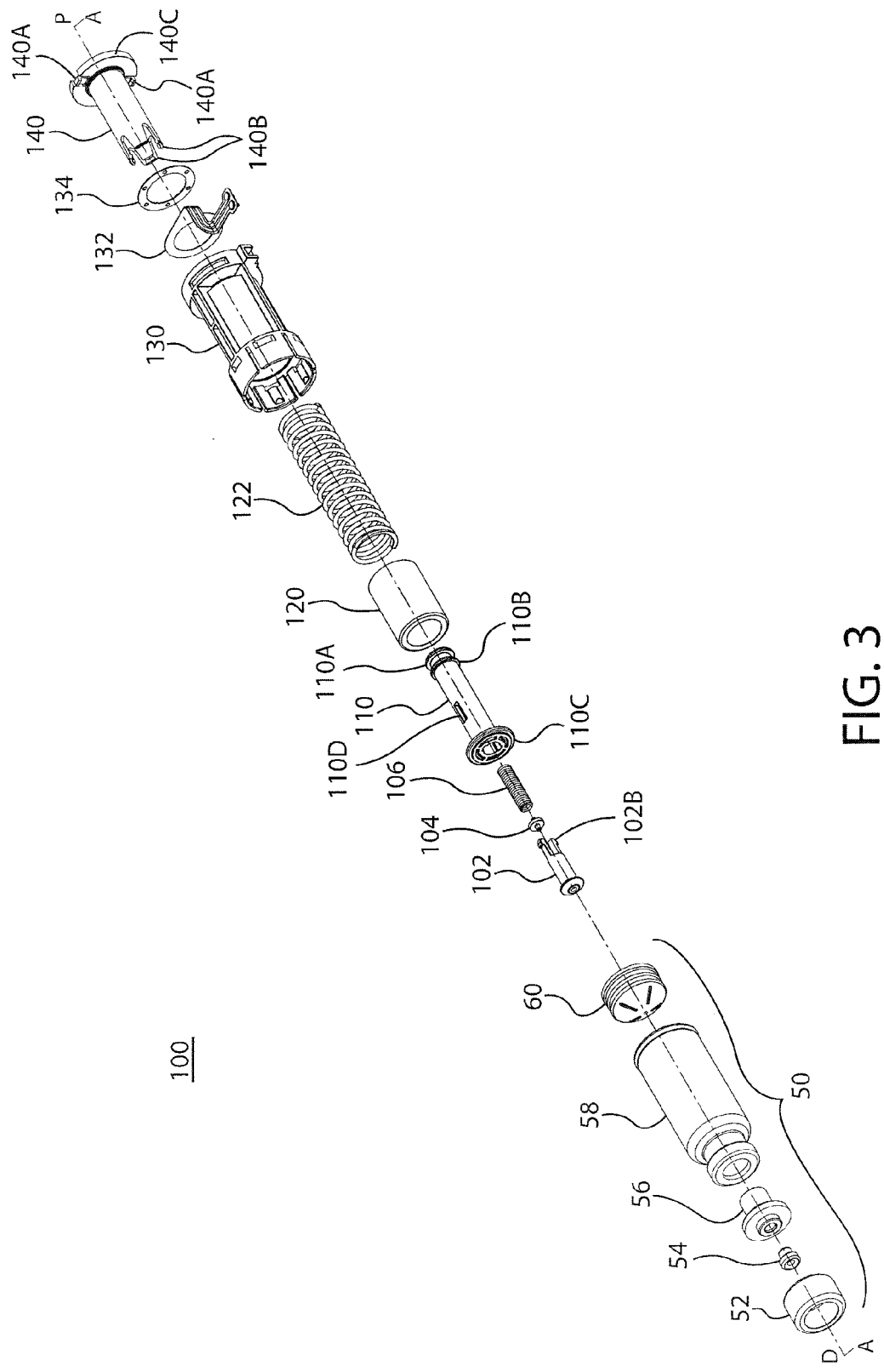
FIG. 3 shows an exploded view, along an axis "A," of the drive mechanism shown in FIG. 2.

Drive Mechanism:

With reference to the embodiments shown in FIGS. 2 and 3, drive mechanism 100 includes a drive housing 130, a status switch interconnect 132, and a drug container 50 having a cap 52, a pierceable seal 56, a barrel 58, and a plunger seal 60. The drug container may contain a drug fluid, within the barrel between the pierceable seal and the plunger seal, for delivery through the insertion mechanism and drug pump into the body of the user. The seals described herein may be comprised of a number of materials but are, in a preferred embodiment, comprised of one or more elastomers or rubbers. The drive mechanism may further include a connection mount 54 to guide the insertion of the piercing member of the fluid pathway connection into the barrel 58 of the drug container 50. The drive mechanism 100 may further contain one or more drive biasing members, one or more release mechanisms, and one or more guides, as are described further herein. The components of the drive mechanism function to force a fluid from the drug container out through the pierceable seal, or preferably through the piercing member of the fluid pathway connection, for delivery through the fluid pathway connection, sterile fluid conduit, and insertion mechanism into the body of the user.

The drive mechanism may further include one or more contact surfaces located on corresponding components. Such contact surfaces may be electrical contact surfaces, mechanical contact surfaces, or electro-mechanical contact surfaces. Such surfaces may initially be in contact and caused to disengage, or initially be disconnected and caused to engage, to permit a signal to be sent to and/or from the power control system 400. In at least one embodiment, as described further herein, the contact surfaces may be electrical contact surfaces which are initially disconnected and caused to come into engagement whereby, upon such engagement, contact surfaces are capable of continuing an energy pathway or otherwise relaying a signal to the power and control system 400. In another embodiment of the present invention, the contact surfaces are mechanical contact surfaces which are initially in contact and caused to disengage whereby, upon such disengagement, such disengagement is communicated to the power and control system 400. Such signals may be transferred across one or more interconnects 132 to the power and control system 400 or by mechanical action to the power and control system 400. Such components may be utilized within the drive mechanism to measure and relay information related to the status of operation of the drive mechanism, which may be converted by the power and control system 400 into tactile, auditory, and/or visual feedback to the user. Such embodiments are described further herein. Regardless of the electrical or mechanical nature of the contact surfaces, the motion of the components which permits transmission of a signal to the power control system 400 is enabled by a biasing member 122 axially translating a contact sleeve 140 in the distal direction during operation of the device.

In one particular embodiment, the drive mechanism 100 employs one or more compression springs as the biasing member(s). Upon activation of the drug pump by the user, the power and control system may be actuated to directly or indirectly release the compression spring(s) from an energized state. Upon release, the compression spring(s) may bear against and act upon the plunger seal to force the fluid drug out of the drug container. The fluid pathway connection may be connected through the pierceable seal prior to, concurrently with, or after activation of the drive mechanism to permit fluid flow from the drug container, through the fluid pathway connection, sterile fluid conduit, and insertion mechanism, and into the body of the user for drug delivery. In at least one embodiment, the fluid flows through only a manifold and a cannula of the insertion mechanism, thereby maintaining the sterility of the fluid pathway before and during drug delivery. Such components and their functions are described in further detail hereinafter.

Referring now to the embodiment of the drive mechanism shown in FIG. 3, the drive mechanism 100 includes a drug container 50 having a cap 52, a pierceable seal 56, a barrel 58, and a plunger seal 60, and optionally a connection mount 54. The drug container 50 is mounted to a distal end of a drive housing 130. Compressed within the drive housing 130, between the drug container 50 and the proximal end of the housing 130, are a drive biasing member 122 and a piston 110, wherein the drive biasing member 122 is configured to bear upon an interface surface 110C of the piston 110, as described further herein. Optionally, a cover sleeve 120 may be utilized between the drive biasing member 122 and the interface surface 110C of the piston 110 to, for example, promote more even distribution of force from the drive biasing member 122 to the piston 110, prevent buckling of the drive biasing member 122, and/or hide biasing member from user view. Interface surface 110C of piston 110 is caused to rest substantially adjacent to, or in contact with, a proximal end of seal 60.

The drive mechanism 100 further includes, mounted at a distal end, a status switch interconnect 132. A contact sleeve 140 is slidably mounted to the drive housing 130 through an axial aperture of the housing 130, such that sleeve hooks 140B at a distal end of the contact sleeve 140 are caused to contact the piston 110 between interface surface 110 and a contact protrusion 110B near the proximal end of the piston 110. Piston 110 also includes a locking groove 110A, between contact protrusion 110B and the proximal end of the piston 110. Contact sleeve 140 has a radially extending ring 140C at its proximal end, upon which resides one or more flex prongs 140A. An electrical contact 134 may be connected, mounted, printed, or otherwise mounted to ring 140C which, during operation of the drive mechanism, may come in contact with corresponding status switch interconnect 132 to complete an electrical circuit or otherwise permit a transmission to the power and control system to provide feedback to the user.

The components of the drive mechanism 100, upon activation, may be used to drive axial translation in the distal direction of the plunger seal 60 of the drug container 50. Optionally, the drive mechanism 100 may include one or more compliance features which enable additional axial translation of the plunger seal 60 to, for example, ensure that substantially the entire drug dose has been delivered to the user and make sure that the feedback contact mechanisms have connected. For example, in one embodiment of the present invention, the sleeve hooks 140B are flex arms which may permit, upon sufficient application of force by the drive biasing member 122 on the piston 110, to allow interface surface 110C to translate axially beyond sleeve hooks 140B to drive further axial translation of the plunger seal 60 for a compliance push of drug fluid from the drug container. Additionally or alternatively, the plunger seal 60, itself, may have some compressibility permitting a compliance push of drug fluid from the drug container.

In at least one embodiment of the present invention, a compliance push of drug fluid from the drug container is enabled by a piston extension 102. In such embodiments, the drive mechanism 100 further includes a piston extension 102 slidably mounted at a distal end and within an axial pass-through of piston 110. The piston extension 102 may be retained within piston 110 by interaction between extension arms 102B of the piston extension 102 and connection slots 110D of piston 110, as shown in FIGS. 4A-4E. Piston extension may be driven by a piston extension biasing member 106, which is mounted within the axial pass-through of piston 110 and initially compressed between piston extension 102 and piston 110. An optional piston biasing member support 104 may be utilized between piston extension biasing member 106 and piston extension 102 to, for example, promote more uniform distribution of force from piston extension biasing member 106 to piston extension 102. The function of the optional piston extension is described in further detail hereinafter.

The novel drive mechanisms of the present invention integrate status indication into the drug dose delivery. By use of one or more status switch interconnects and one or more corresponding electrical contacts, the status of the drive mechanism before, during, and after operation can be relayed to the power and control system to provide feedback to the user. Such feedback may be tactile, visual, and/or auditory, as described above, and may be redundant such that more than one signals or types of feedback are provided to the user during use of the device. For example, the user may be provided an initial feedback to identify that the system is operational and ready for drug delivery. Upon activation, the system may then provide one or more drug delivery status indications to the user. At completion of drug delivery, the drive mechanism and drug pump may provide an end-of-dose indication. As the end-of-dose indication is tied to the piston reaching the end of its axial translation, the drive mechanism and drug pump provide a true end-of-dose indication to the user.

In at least one embodiment, as shown in FIG. 2 and FIG. 3, an end-of-dose status indication may be provided to the user once the status switch interconnect 132 is caused to contact electrical contact 134 at the end of axial travel of the piston 110 and plunger 60 within the barrel 58 of the drug container 50. In a further embodiment, incremental status indication relaying various stages of drug delivery can be communicated to the user during operation. In one such embodiment, sleeve hooks 140B of cover sleeve 120 may have one or more interconnects which come into contact with one or more electrical contacts on the outer surface of piston 110 during operation.

As piston 110 translates axially in the distal direction to push plunger seal 60 distally, thereby pushing fluid out of the drug container through the pierceable seal end, the electrical contacts of the piston 110 may sequentially contact the interconnect on the sleeve hooks 140B to relay the incremental status of operation. Depending on the number of electrical contacts located on the outer surface of the piston 110, the frequency of the incremental status indication may be varied as desired. The location of the contacts and interconnects may be interchanged or in a number of other configurations which permit completion of an electrical circuit or otherwise permit a transmission between the components.

Figure 6:
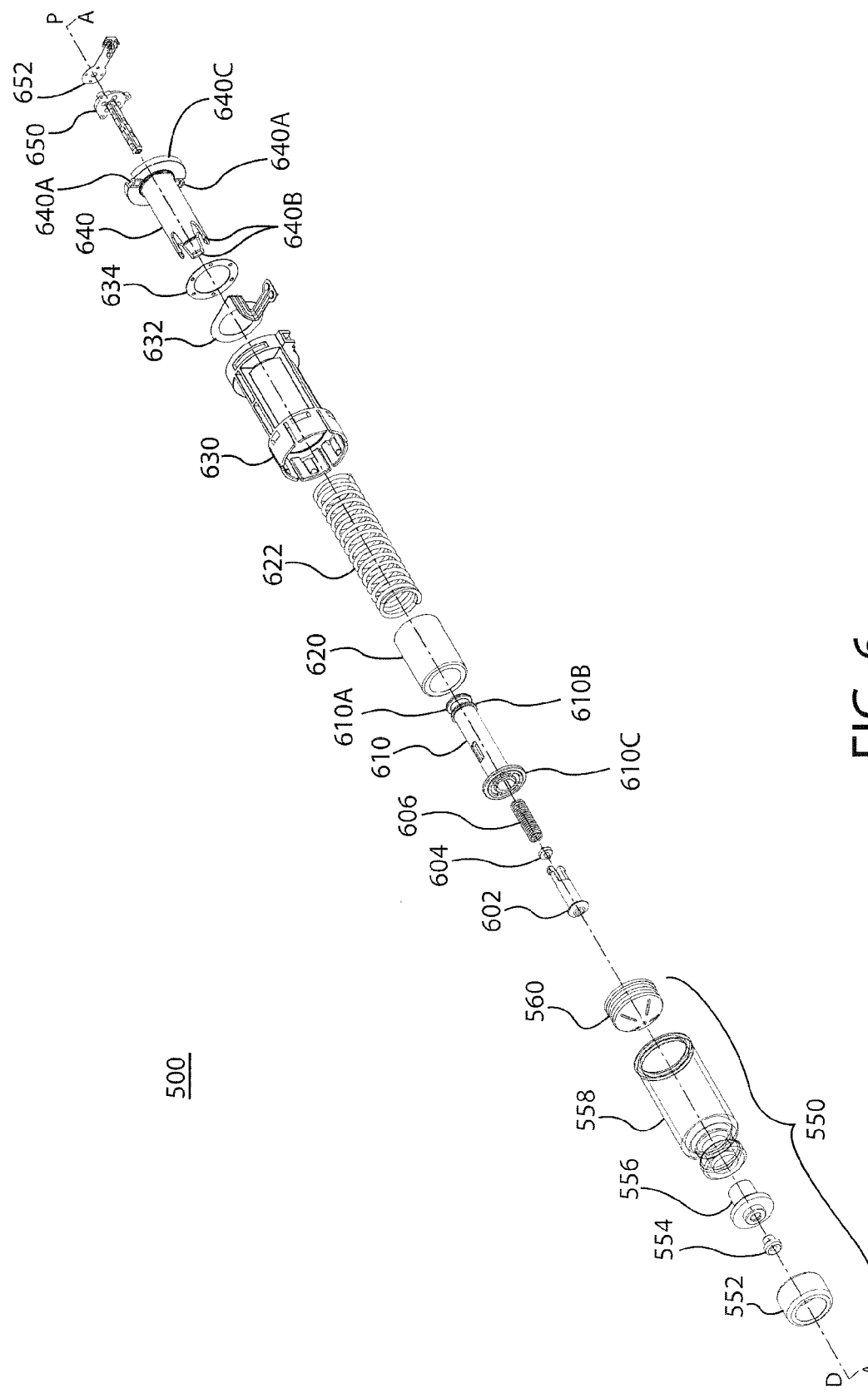
FIG. 6 shows an exploded view, along an axis "A," of the drive mechanism shown in FIG. 5.

In another embodiment of the drive mechanism 500, shown in FIGS. 5 and 6, incremental status indication may be measured and relayed by a separate incremental status stem 650 and a corresponding stem interconnect 652. The stem interconnect 652 may be mounted, affixed, printed, or otherwise attached to incremental status stem 650. Incremental status stem 650 may be a static component, i.e., it does not move or translate, that is mounted to the distal end of contact sleeve 640 and/or the distal end of drive housing 630 such that the incremental status stem 650 resides within an axial pass-through of contact sleeve 640 and drive housing 630. The incremental status stem 650 further resides within an axial pass-through of piston 610. In such embodiments of the present invention, one or more contacts may be located on an inner surface of the piston 610 such that they sequentially interface with one or more corresponding interconnects on the incremental status stem 650. As piston 610 translates axially in the distal direction to push plunger seal 60 distally, thereby pushing fluid out of the drug container through the pierceable seal end, the electrical contacts of the piston 610 may sequentially contact the interconnect on the incremental status stem 650 to relay the incremental status of operation. Depending on the number of electrical contacts, the frequency of the incremental status indication may be varied as desired. The location of the contacts and interconnects may be interchanged or in a number of other configurations which permit completion of an electrical circuit or otherwise permit a transmission between the components.

Figure 7:
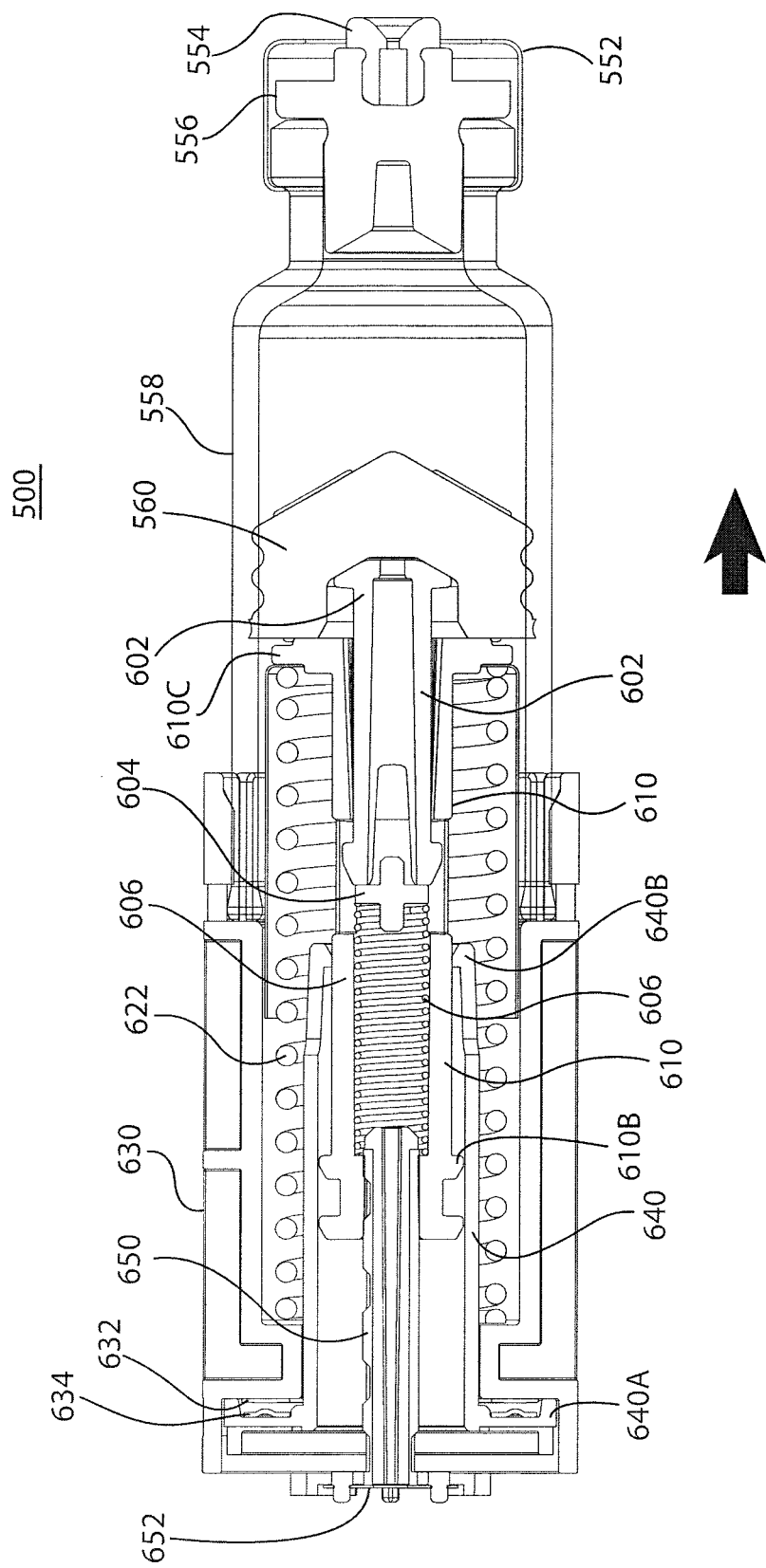
FIG. 7 shows a cross-sectional view of the drive mechanism shown in FIG. 5 in an actuated state.

FIG. 7 shows a cross-sectional view of the embodiment of the drive mechanism shown in FIG. 5 during operation of the drive mechanism. As shown, incremental status stem 650 may be a static component that is mounted to the distal end of contact sleeve 640 and/or the distal end of drive housing 630 such that the incremental status stem 650 resides within an axial pass-through of contact sleeve 640 and drive housing 630. As piston 610 translates axially in the distal direction (i.e., in the direction of the solid arrow) to push plunger seal 60 distally, the electrical contacts of the piston 610 may sequentially contact the interconnect on the incremental status stem 650 to relay the incremental status of operation through stem interconnect 652. Accordingly, incremental status of the drive mechanism, and therefore status of drug delivery, may be conveyed to the user during use of the device.

Figure 4A:
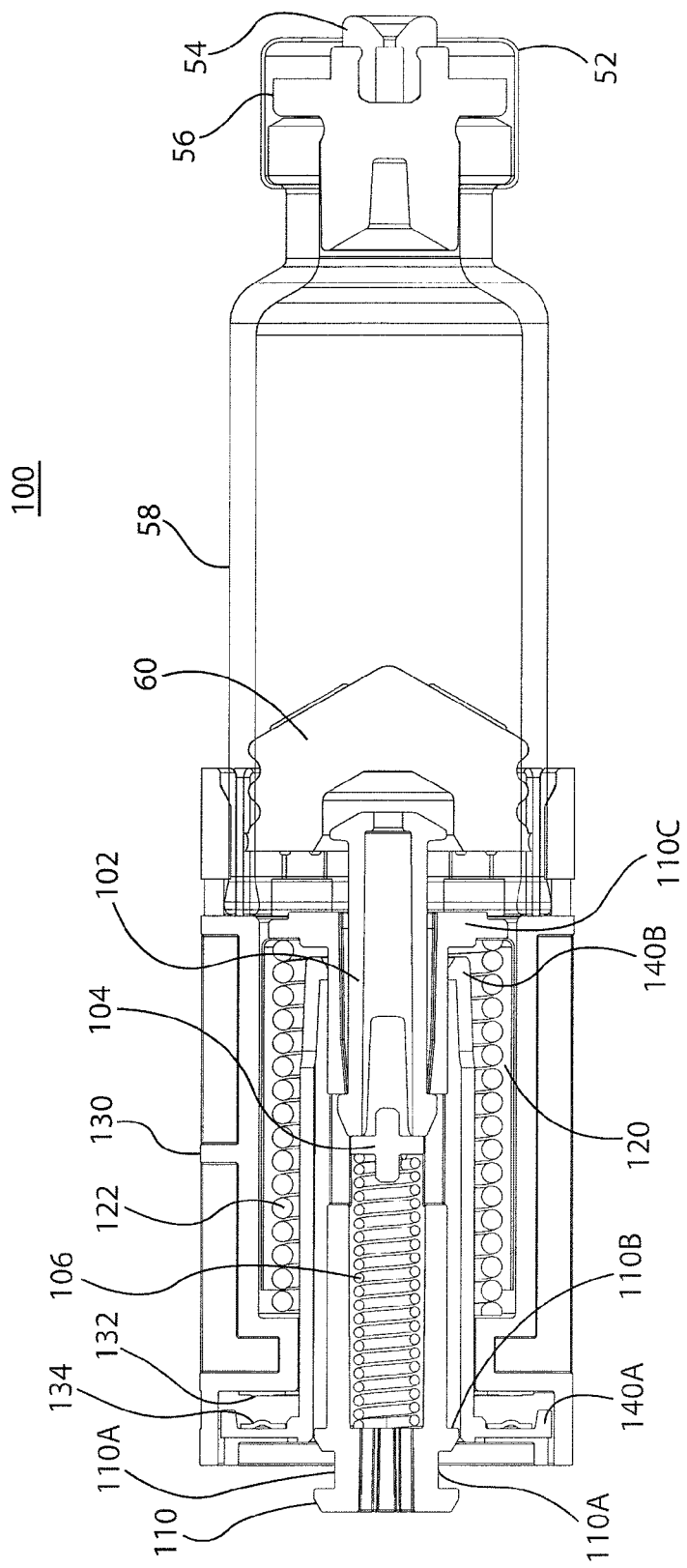
FIG. 4A shows a cross-sectional view of the drive mechanism shown in FIG. 2 in an initial inactive state.

Returning now to the embodiment shown in FIGS. 2-3, further aspects of the novel drive mechanism will be described with reference to FIGS. 4A-4E. One or more of these aspects may similarly be utilized in the embodiment shown in FIG. 5, or any other variation captured by the embodiments described herein. FIG. 4A shows a cross-sectional view of the drive mechanism, according to at least a first embodiment, during its initial locked stage. A fluid, such as a drug fluid, may be contained within barrel 58 between plunger seal 60 and pierceable seal 56, for delivery to a user. Upon activation by the user, a fluid pathway connection may be connected to the drug container through the pierceable seal 56. As described above, this fluid connection may be facilitated by a piercing member of the fluid pathway connection which pierces the pierceable seal and completes the fluid pathway from the drug container, through the fluid pathway connection, the fluid conduit, the insertion mechanism, and the cannula for delivery of the drug fluid to the body of the user. Initially, one or more locking mechanisms (not shown) may reside within the locking grooves 110A of piston 110. Directly or indirectly upon activation of the device by the user, the locking mechanism may be removed from the locking grooves 110A of piston 110, to permit operation of the drive mechanism.

Figure 4B:
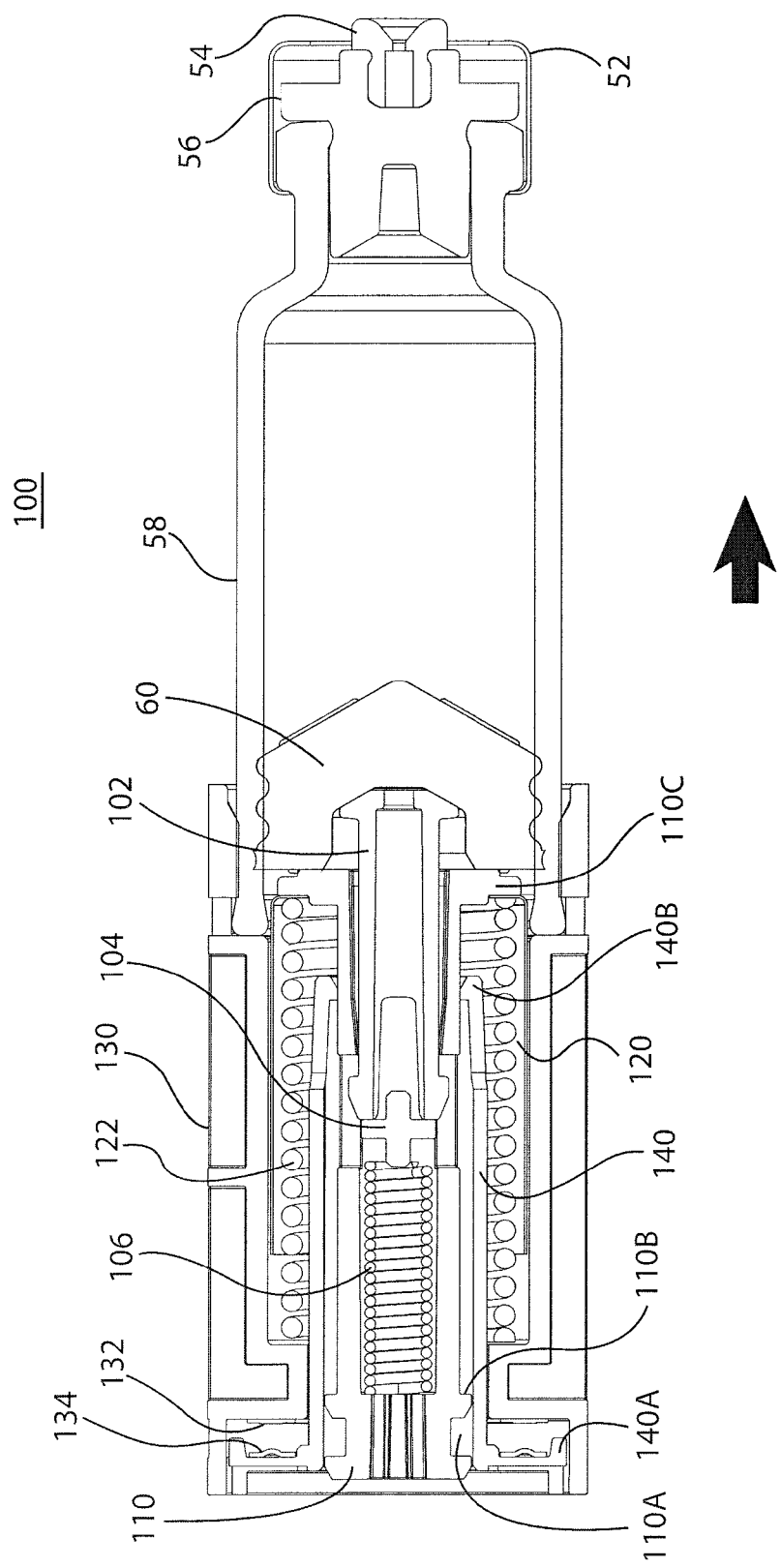
FIG. 4B shows a cross-sectional view of the drive mechanism shown in FIG. 2 in an actuated state.
Figure 4C:
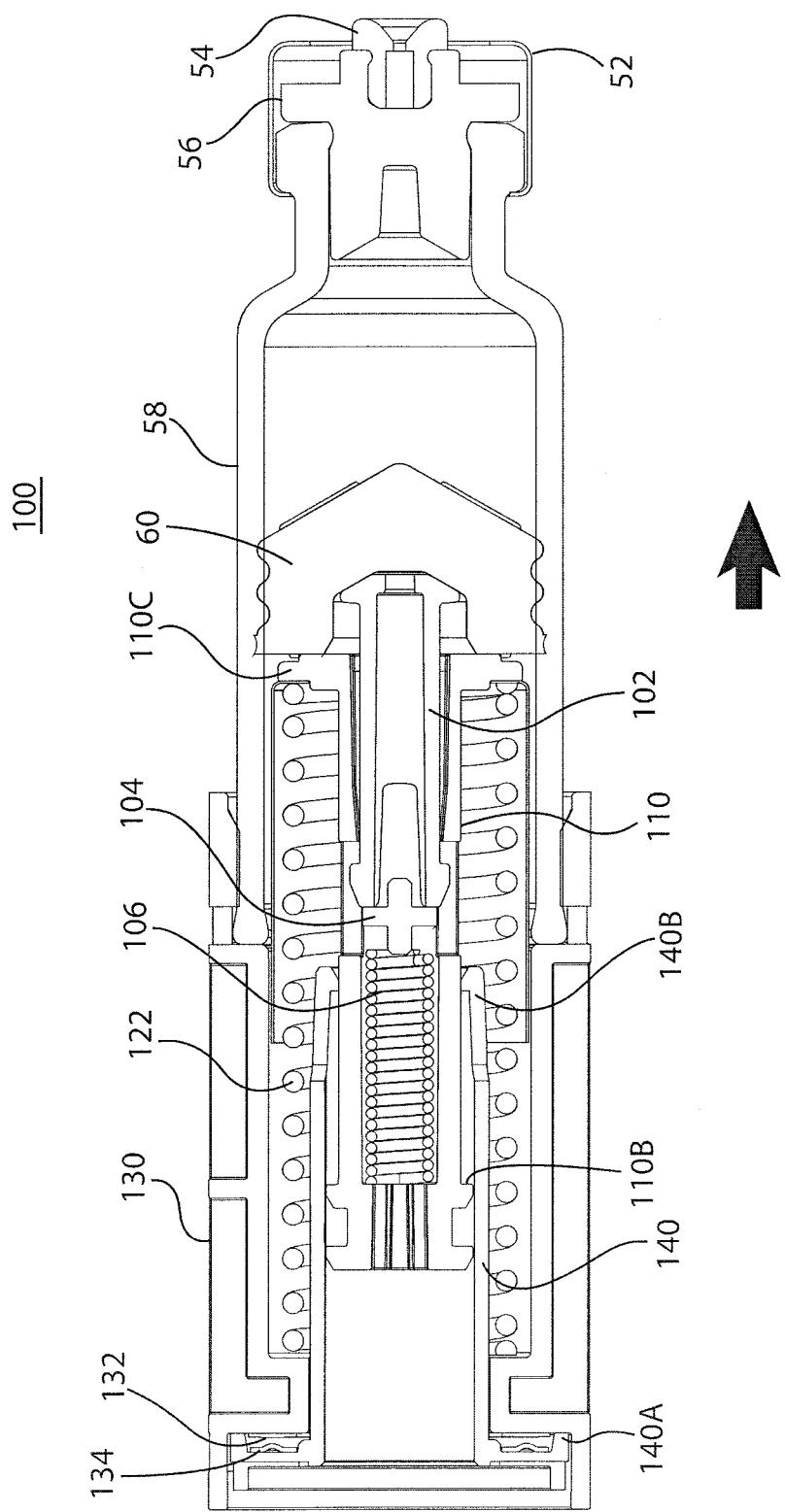
FIG. 4C shows a cross-sectional view of the drive mechanism shown in FIG. 2 in a further actuated state as drug delivery from the mechanism continues.

As shown in FIG. 4A, the piston extension biasing member 106 and drive biasing member 122 are both initially in a compressed, energized state. The drive biasing member 122 may be maintained in this state until activation of the device between internal features of drive housing 130 and interface surface 110C of piston 110. As the locking mechanism is removed from the locking groove 110A of piston 110, drive biasing member 122 is permitted to expand (i.e., decompress) axially in the distal direction (i.e., in the direction of the solid arrow). Such expansion causes the drive biasing member 122 to act upon and distally translate interface surface 110C and piston 110, thereby distally translating plunger 60 to push drug fluid out of the barrel 58. Distal translation of the piston 110 causes distal translation of the piston extension biasing member 106 and piston extension 102, when such optional features are incorporated into the device. As shown in FIG. 4B, such distal translation of the piston 110 and plunger seal 60 continues to force fluid flow out from barrel 58 through pierceable seal 56. Status switch interconnect 132 is prevented from prematurely contacting electrical contact 134 by one or more flex prongs 140A, as shown in FIG. 4C. Alternatively, low force springs or other resistance mechanisms may be utilized in addition to or alternatively from flex prongs 140A to achieve the same functions. During distal translation of the piston 110, sleeve hooks 140B may slidably contact the outer surface of piston 110. As described above, interconnects and electrical contacts may be located on these components to provide incremental status indication during operation of the drive mechanism.

As the drive mechanism 100 nears or reaches end-of-dose, flex prongs 140A may be caused to flex outwards (i.e., in the direction of the hollow arrows) by the decompression force of drive biasing member 122. Such flexion of the flex prongs 140A may permit status switch interconnect 132 to contact electrical contact 134, completing a circuit or otherwise permitting a transmission to the power and control system to provide feedback to the user. At this stage, one or more delivery compliance mechanisms may be utilized to ensure that the status switch interconnect 132 has contacted electrical contact 134 and/or that substantially the entire drug dose has been delivered. For example, in one embodiment of the present invention, the sleeve hooks 140B are flex arms which may permit, upon sufficient application of force by the drive biasing member 122 on the piston 110, to allow interface surface 110C to translate axially beyond sleeve hooks 140B to drive further axial translation of the plunger seal 60 for a compliance push of drug fluid from the drug container. Additionally or alternatively, the plunger seal 60, itself, may have some compressibility permitting a compliance push of drug fluid from the drug container. For example, when a pop-out plunger seal is employed, i.e., a plunger seal that is deformable from an initial state, the plunger seal may be caused to deform or "pop-out" to provide a compliance push of drug fluid from the drug container.

Figure 4D:
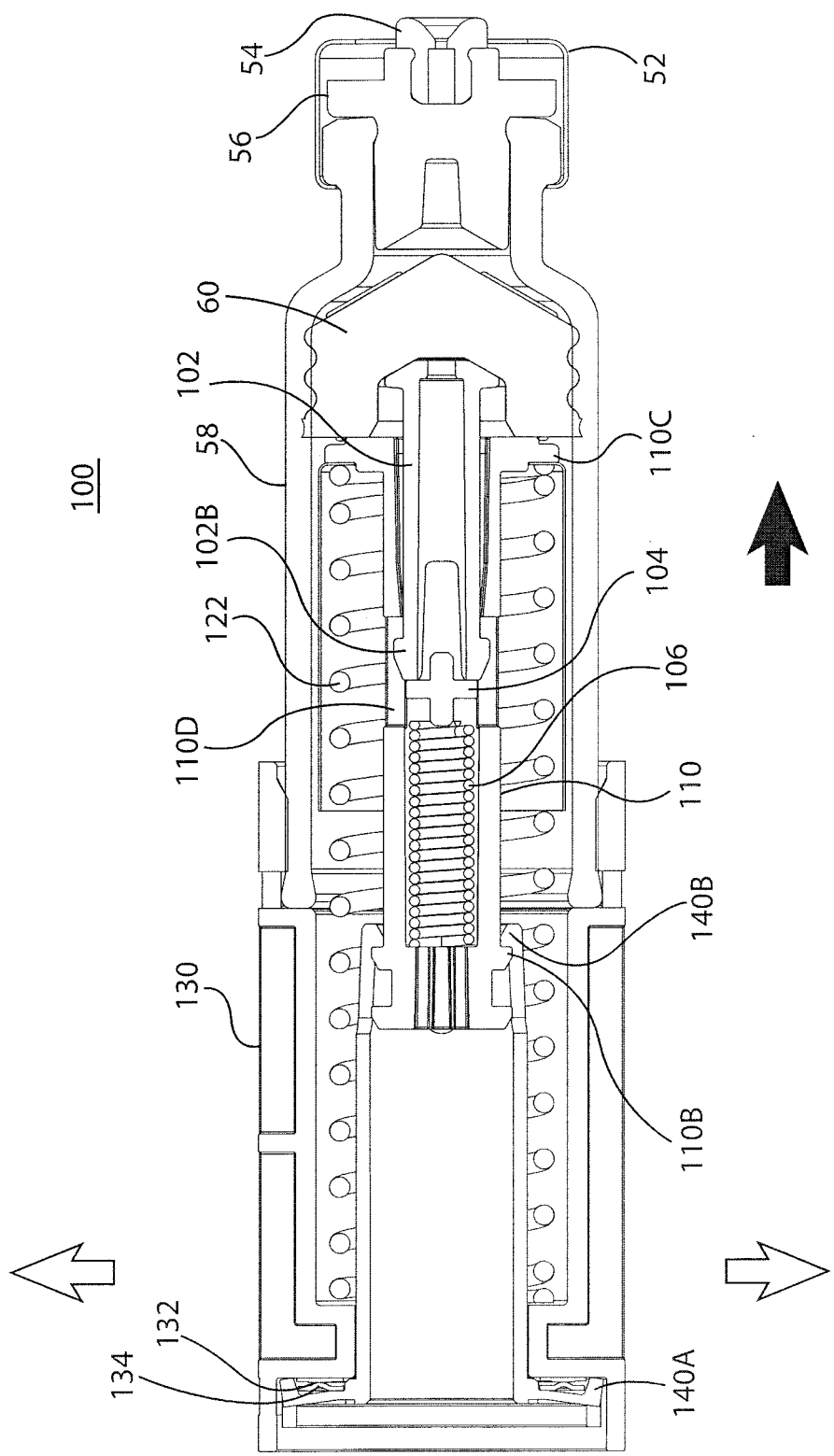
FIG. 4D shows a cross-sectional view of the drive mechanism shown in FIG. 2 as the mechanism nears completion of drug delivery.

In at least one embodiment of the present invention, a compliance push of drug fluid from the drug container is enabled by a piston extension 102. In such embodiments, the drive mechanism 100 further includes a piston extension 102 slidably mounted at a distal end and within an axial pass-through of piston 110. The piston extension 102 may be retained within piston 110 by interaction between extension arms 102B of the piston extension 102 and connection slots 110D of piston 110, as shown in FIG. 4D. Piston extension may be driven by a piston extension biasing member 106, which is mounted within the axial pass-through of piston 110 and initially compressed between piston extension 102 and piston 110. An optional piston biasing member support 104 may be utilized between piston extension biasing member 106 and piston extension 102 to, for example, promote more uniform distribution of force from piston extension biasing member 106 to piston extension 102.

Figure 4E:
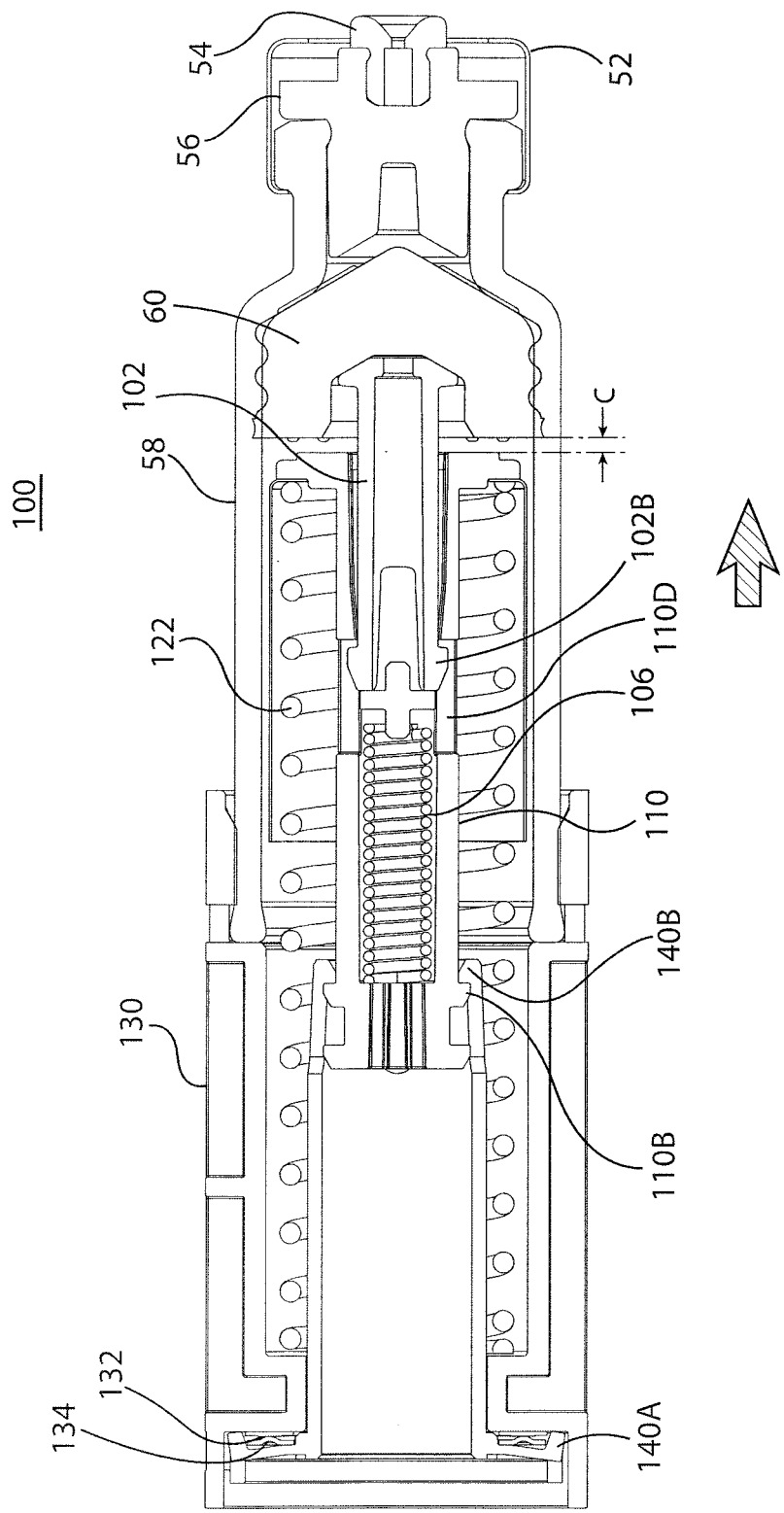
FIG. 4E shows a cross-sectional view of the drive mechanism shown in FIG. 2 as the mechanism performs a compliance push to ensure completion of drug delivery.

As the piston 110 reaches its end of travel within barrel 58, piston extension 102 may be permitted to axially travel in the distal direction by the force exerted by piston extension biasing member 106. At this stage, the piston extension biasing member 106 is permitted to expand (i.e., decompress) axially in the distal direction such that extension arms 102B of the piston extension 102 may translate distally (i.e., in the direction of the solid arrow) within connection slots 110D of piston 110, as shown in FIG. 4D. As shown in FIG. 4E, such distal translation (i.e., in the direction of the hatched arrow) of the piston extension 102 enables a compliance push (shown by dimension "C" in FIG. 4E) of drug fluid from the drug container. Piston extension 102 may be configured such that extension arms 102B may contact and apply force upon a distal end of connections slots 110D to distally translate piston 110 further (i.e., in the direction of the hatched arrow). This further distal translation of the piston 110 may be utilized to ensure that status switch interconnect 132 has engaged contact 134.

As described above, the novel drive mechanisms of the present invention integrate status indication into the drug dose delivery. Through integration of the end-of-dose status indication mechanisms to the axial translation of the piston, and thereby the plunger seal, true and accurate end-of-dose indication may be provided to the user. By use of one or more contact surfaces on corresponding components, the status of the drive mechanism before, during, and after operation can be relayed to the power and control system to provide feedback to the user. Such feedback may be tactile, visual, and/or auditory, as described above, and may be redundant such that more than one signals or types of feedback are provided to the user during use of the device. FIGS. 4A-4E above show an arrangement which provide end-of-dose status indication to the user once the status switch interconnect 132 is caused to contact electrical contact 134 at the end of axial travel of the piston 110 and plunger 60 within the barrel 58 of the drug container 50. As described above, the novel devices described herein may additionally provide incremental status indication to relay various stages of drug delivery to the user during operation. In one such embodiment, sleeve hooks 140B of cover sleeve 120 may have one or more interconnects which come into contact with one or more electrical contacts on the outer surface of piston 110 during operation. A redundant end-of-dose indication may be utilized upon contact between sleeve hooks 140B of contact sleeve 140 and contact protrusion 110B of piston 110. Electrical contacts or interconnects along piston 110 may sequentially contact the corresponding interconnects or contacts on the sleeve hooks 140B to relay the incremental status of operation. Depending on the number of electrical contacts located on the outer surface of the piston 110, the frequency of the incremental status indication may be varied as desired. The location of the contacts and interconnects may be interchanged or in a number of other configurations which permit completion of an electrical circuit or otherwise permit a transmission between the components.

In another embodiment of the drive mechanism 500, shown in FIGS. 5-7, incremental status indication may be measured and relayed by a separate incremental status stem 650 and a corresponding stem interconnect 652. As shown in FIG. 7, incremental status stem 650 may be a static component that is mounted to the distal end of contact sleeve 640 and/or the distal end of drive housing 630 such that the incremental status stem 650 resides within an axial pass-through of contact sleeve 640 and drive housing 630. As piston 610 translates axially in the distal direction (i.e., in the direction of the solid arrow) to push plunger seal 60 distally, the electrical contacts of the piston 610 may sequentially contact the interconnect on the incremental status stem 650 to relay the incremental status of operation through stem interconnect 652. Depending on the number of electrical contacts, the frequency of the incremental status indication may be varied as desired. The location of the contacts and interconnects may be interchanged or in a number of other configurations which permit completion of an electrical circuit or otherwise permit a transmission between the components. Accordingly, incremental status of the drive mechanism, and therefore status of drug delivery, may be conveyed to the user during use of the device.

In a further embodiment of the drive mechanism, shown in FIGS. 8 and 9A-9C, drive mechanism 1000 may be similar to mechanism 100 or mechanism 500, and incorporate the respective components and functions of such embodiments, but utilize mechanical contact surfaces instead of electrical contact surfaces, as described above. FIG. 8 shows an isometric view of the drive mechanism 1000 according to a further embodiment of the present invention. FIGS. 9A-9C show cross-sectional views of the drive mechanism shown in FIG. 8 in an initial inactive state, an actuated state and as the mechanism nears completion of drug delivery, and as the mechanism completes drug delivery and triggers an end-of-dose signal. In such embodiments, the status switch interconnect is a mechanical trigger 1150 and the contact surface is a pin 1140P. As shown in FIG. 9A, the optional piston extension biasing member 1106 and drive biasing member 1122 are both initially in a compressed, energized state. The drive biasing member 1122 may be maintained in this state until activation of the device between internal features of drive housing 1130 and interface surface 1110C of piston 1110. As the locking mechanism is removed from the locking groove 1110A of piston 1110, drive biasing member 1122 is permitted to expand (i.e., decompress) axially in the distal direction (i.e., in the direction of the solid arrow). Such expansion causes the drive biasing member 1122 to act upon and distally translate interface surface 1110C and piston 1110, thereby distally translating plunger 1060 to push drug fluid out of the barrel 1058. Distal translation of the piston 1110 causes distal translation of the piston extension biasing member 1106 and piston extension 1102, when such optional features are incorporated into the device.

As shown in FIG. 9B, such distal translation of the piston 1110 and plunger seal 1060 continues to force fluid flow out from barrel 1058 through pierceable seal 1056. As described above, interconnects and electrical contacts may be located on these components to provide incremental status indication during operation of the drive mechanism. As shown in FIG. 9C, as the drive mechanism 1000 reaches end-of-dose, pin 1140P disengages from mechanical trigger 1150 to permit a transmission to the power and control system 400 to provide feedback to the user. In one such embodiment, disengagement of the pin 1140P from the mechanical trigger 1150 permits the trigger to rotate as it is biased by a biasing member, such as a constant-force spring 1170. Initially, the constant-force spring 1170 biases the mechanical trigger 1150 against the pin 1140P. Upon axial translation of the pin 1140P, as described above, pin 1140P disengages from mechanical trigger 1150 which then rotates or is otherwise displaced to permit transmission of feedback to the user. At this stage, one or more delivery compliance mechanisms, as described above, may be utilized to ensure that the pin 1140P has disengaged mechanical trigger 1150 and/or that substantially the entire drug dose has been delivered.

Assembly and/or manufacturing of drive mechanism 100, drug delivery pump 10, or any of the individual components may utilize a number of known materials and methodologies in the art. For example, a number of known cleaning fluids such as isopropyl alcohol and hexane may be used to clean the components and/or the devices. A number of known adhesives or glues may similarly be employed in the manufacturing process. Additionally, known siliconization and/or lubrication fluids and processes may be employed during the manufacture of the novel components and devices. Furthermore, known sterilization processes may be employed at one or more of the manufacturing or assembly stages to ensure the sterility of the final product.

The drive mechanism may be assembled in a number of methodologies. In one method of assembly, the drug container 50 may first be assembled and filled with a fluid for delivery to the user. The drug container 50 includes a cap 52, a pierceable seal 56, a barrel 58, and a plunger seal 60. The pierceable seal 56 may be fixedly engaged between the cap 52 and the barrel 58, at a distal end of the barrel 58. The barrel 58 may be filled with a drug fluid through the open proximal end prior to insertion of the plunger seal 60 from the proximal end of the barrel 58. An optional connection mount 54 may be mounted to a distal end of the pierceable seal 56. The connection mount 54 to guide the insertion of the piercing member of the fluid pathway connection into the barrel 58 of the drug container 50. The drug container 50 may then be mounted to a distal end of drive housing 130.

One or more switch status interconnects 132 may be mounted to a proximal end of drive housing 130. A contact sleeve 140, having one or more sleeve hooks 140B at a distal end and a ring 140C at a proximal end having an electrical contact 134 thereon, may be mounted to the drive housing 130 through an axial pass-through from the proximal end of the drive housing 130. A drive biasing member 122 may be inserted into a distal end of the drive housing 130. Optionally, a cover sleeve 120 may be inserted into a distal end of the drive housing 130 to substantially cover biasing member 122. A piston may be inserted into the distal end of the drive housing 130 and through an axial pass-through of contact sleeve 140, such that a contact protrusion 110B of piston 110 is proximal to the sleeve hooks 140B of contact sleeve 140. The piston 110 and drive biasing member 122, and optional cover sleeve 120, may be compressed into drive housing 130. Such assembly positions the drive biasing member 122 in an initial compressed, energized state and preferably places a piston interface surface 110C in contact with the proximal surface of the plunger seal 60 within the proximal end of barrel 58. When a piston extension 102 is employed, the piston extension 102 and piston extension biasing member 106, and optional piston biasing member support, may be compressed into an axial pass-through of piston 110. The piston, piston biasing member, contact sleeve, and optional components, may be compressed and locked into the ready-to-actuate state within the drive housing 130 prior to attachment or mounting of the drug container 50.

When one or more interconnects or contacts are utilized for status indication, such components may be mounted, connected, printed, or otherwise attached to their corresponding components prior to assembly of such components into the drive mechanism 100. When a separate incremental status stem 650 and a corresponding stem interconnect 652 are utilized for such incremental status indication, the stem interconnect 652 may be mounted, affixed, printed, or otherwise attached to incremental status stem 650. The incremental status stem 650 and stem interconnect 652 to the proximal end of the contact sleeve 640 and/or the proximal end of the drive housing 630 in a manner such that the incremental status stem 650 resides within an axial pass-through of contact sleeve 640 and drive housing 630. The incremental status stem 650 is further mounted to reside within an axial pass-through of piston 610.

A fluid pathway connection, and specifically a sterile sleeve of the fluid pathway connection, may be connected to the cap and/or pierceable seal of the drug container. A fluid conduit may be connected to the other end of the fluid pathway connection which itself is connected to the insertion mechanism such that the fluid pathway, when opened, connected, or otherwise enabled travels directly from the drug container, fluid pathway connection, fluid conduit, insertion mechanism, and through the cannula for drug delivery into the body of a user. The components which constitute the pathway for fluid flow are now assembled. These components may be sterilized, by a number of known methods, and then mounted either fixedly or removably to an assembly platform or housing of the drug pump, as shown in FIG. 1B.

Certain optional standard components or variations of drive mechanism 100 or drug pump 10 are contemplated while remaining within the breadth and scope of the present invention. For example, upper or lower housings may optionally contain one or more transparent or translucent windows 18, as shown in FIG. 1A, to enable the user to view the operation of the drug pump 10 or verify that drug dose has completed. Additionally, the drug pump 10 may contain an adhesive patch 26 and a patch liner 28 on the bottom surface of the housing 12. The adhesive patch 26 may be utilized to adhere the drug pump 10 to the body of the user for delivery of the drug dose. As would be readily understood by one having ordinary skill in the art, the adhesive patch 26 may have an adhesive surface for adhesion of the drug pump to the body of the user. The adhesive surface of the adhesive patch 26 may initially be covered by a non-adhesive patch liner 28, which is removed from the adhesive patch 26 prior to placement of the drug pump 10 in contact with the body of the user. Removal of the patch liner 28 may further remove the sealing membrane 254 of the insertion mechanism 200, opening the insertion mechanism to the body of the user for drug delivery (as shown in FIG. 1C).

Similarly, one or more of the components of drive mechanism 100 and drug pump 10 may be modified while remaining functionally within the breadth and scope of the present invention. For example, as described above, while the housing of drug pump 10 is shown as two separate components upper housing 12A and lower housing 12B, these components may be a single unified component. Similarly, while electrical contact 134 is shown as a separate component from contact sleeve 140, it may be a unified component printed onto the ring surface of the contact sleeve 140. As discussed above, a glue, adhesive, or other known materials or methods may be utilized to affix one or more components of the drive mechanism and/or drug pump to each other. Alternatively, one or more components of the drive mechanism and/or drug pump may be a unified component. For example, the upper housing and lower housing may be separate components affixed together by a glue or adhesive, a screw fit connection, an interference fit, fusion joining, welding, ultrasonic welding, and the like; or the upper housing and lower housing may be a single unified component. Such standard components and functional variations would be appreciated by one having ordinary skill in the art and are, accordingly, within the breadth and scope of the present invention.

It will be appreciated from the above description that the drive mechanisms and drug pumps disclosed herein provide an efficient and easily-operated system for automated drug delivery from a drug container. The novel embodiments described herein provide integrated status indication to provide feedback to the user. The novel drive mechanisms of the present invention may be directly or indirectly activated by the user. For example, in at least one embodiment the lockout pin(s) which maintain the drive mechanism in its locked, energized state are directly displaced from the corresponding lockout grooves of the piston 110 by user depression of the activation mechanism. Furthermore, the novel configurations of the drive mechanism and drug pumps of the present invention maintain the sterility of the fluid pathway during storage, transportation, and through operation of the device. Because the path that the drug fluid travels within the device is entirely maintained in a sterile condition, only these components need be sterilized during the manufacturing process. Such components include the drug container of the drive mechanism, the fluid pathway connection, the sterile fluid conduit, and the insertion mechanism. In at least one embodiment of the present invention, the power and control system, the assembly platform, the control arm, the activation mechanism, the housing, and other components of the drug pump do not need to be sterilized. This greatly improves the manufacturability of the device and reduces associated assembly costs. Accordingly, the devices of the present invention do not require terminal sterilization upon completion of assembly. A further benefit of the present invention is that the components described herein are designed to be modular such that, for example, housing and other components of the pump drug may readily be configured to accept and operate drive mechanism 100, drive mechanism 500, or a number of other variations of the drive mechanism described herein.

Manufacturing of a drug pump includes the step of attaching both the drive mechanism and drug container, either separately or as a combined component, to an assembly platform or housing of the drug pump. The method of manufacturing further includes attachment of the fluid pathway connection, drug container, and insertion mechanism to the assembly platform or housing. The additional components of the drug pump, as described above, including the power and control system, the activation mechanism, and the control arm may be attached, preformed, or pre-assembled to the assembly platform or housing. An adhesive patch and patch liner may be attached to the housing surface of the drug pump that contacts the user during operation of the device.

A method of operating the drug pump includes the steps of: activating, by a user, the activation mechanism; displacing a control arm to actuate an insertion mechanism; and actuating a power and control system to activate a drive control mechanism to drive fluid drug flow through the drug pump. The method may further include the step of: engaging an optional on-body sensor prior to activating the activation mechanism. The method similarly may include the step of: establishing a connection between a fluid pathway connection to a drug container. Furthermore, the method of operation may include translating a plunger seal within the drive control mechanism and drug container to force fluid drug flow through the drug container, the fluid pathway connection, a sterile fluid conduit, and the insertion mechanism for delivery of the fluid drug to the body of a user. The method of operation of the insertion mechanism and the drug pump may be better appreciated with reference to FIGS. 4A-4E, as described above.

Throughout the specification, the aim has been to describe the preferred embodiments of the invention without limiting the invention to any one embodiment or specific collection of features. Various changes and modifications may be made to the embodiments described and illustrated without departing from the present invention. The disclosure of each patent and scientific document, computer program and algorithm referred to in this specification is incorporated by reference in its entirety.

What is claimed is:

1. A drive mechanism having integrated status indication comprises: a drive housing, a status switch interconnect, a drive biasing member including at least one spring, a piston, a contact sleeve slidably mounted to the drive housing through an axial aperture of the drive housing, and a drug container having a cap, a pierceable seal, a barrel, and a plunger seal, wherein the drive biasing member is configured to bear upon an interface surface of the piston and sleeve hooks at a distal end of the contact sleeve are caused to contact the piston between interface surface and a contact protrusion near the proximal end of the piston.

2. The drive mechanism of claim 1, wherein the drug container contains a drug fluid.

3. The drive mechanism of claim 1 further comprising a connection mount attached to the pierceable seal.

4. The drive mechanism of claim 1, further including a cover sleeve disposed between the drive biasing member and the interface surface of the piston.

5. The drive mechanism of claim 1, wherein the piston also includes a locking groove, between contact protrusion and the proximal end of the piston.

6. A drug delivery pump with integrated status indication comprises a housing and an assembly platform, upon which an activation mechanism, an insertion mechanism, a fluid pathway connection, a power and control system, and a drive mechanism having a drug container may be mounted, said drive mechanism comprising: a drive housing, a status switch interconnect, a drive biasing member including at least one spring, a piston, a contact sleeve slidably mounted to the drive housing through an axial aperture of the drive housing, and a drug container having a cap, a pierceable seal, a barrel, and a plunger seal, wherein the drive biasing member is configured to bear upon an interface surface of the piston and sleeve hooks at a distal end of the contact sleeve are caused to contact the piston between the interface surface and a contact protrusion near the proximal end of the piston.

7. The drug delivery pump of claim 6, wherein the drug container contains a drug fluid.

8. The drug delivery pump of claim 6, further including a cover sleeve disposed between the drive biasing member and the interface surface of the piston.

9. The drug delivery pump of claim 6, wherein the piston also includes a locking groove, between contact protrusion and the proximal end of the piston.

10. The drug delivery pump of claim 6 further comprising a piston extension slidably mounted at a distal end and within an axial pass-through of the piston; a piston extension biasing member, which is mounted within the axial pass-through of the piston and initially compressed between the piston extension and the piston; wherein the piston extension is retained within the piston by interaction between one or more extension arms of the piston extension and one or more corresponding connection slots of the piston.

11. The drug delivery pump of claim 10 further including a piston biasing member support between piston extension biasing member and piston extension.

12. A drive mechanism having integrated status indication comprising:
   a drive housing having an axial aperture,
   a contact sleeve slidably mounted to the drive housing through an axial aperture of the drive housing, the contact sleeve having a contact sleeve proximal end and a contact sleeve distal end, sleeve hooks at the contact sleeve distal end, a radially extending ring at the contact sleeve proximal end, and one or more flex prongs residing on the radially extending ring,
   a status switch interconnect,
   a drive biasing member,
   a piston having proximal end, a contact protrusion near the proximal end of the piston and an interface surface,
   a drug container having a cap, a pierceable seal, a barrel, and a plunger seal,
   wherein the sleeve hooks are caused to contact the piston between the interface surface and the contact protrusion near the proximal end of the piston, the drive biasing member being disposed and configured to bear upon the interface surface of the piston.

13. The drive mechanism of claim 12, wherein a contact may be connected, mounted, printed, or otherwise attached to ring which, during operation of the drive mechanism, may engage with corresponding status switch interconnect to complete a transmission to the power and control system to provide feedback to the user.

14. The drive mechanism of claim 13, wherein the status switch interconnect is an electrical status switch interconnect and the contact is an electrical contact.

15. The drive mechanism of claim 12, wherein a contact may be connected, mounted, printed, or otherwise attached to ring which, during operation of the drive mechanism, may disengage from corresponding status switch interconnect to enable transmission of a signal from the power and control system to provide feedback to the user.

16. A drug delivery pump with integrated status indication comprising the drive mechanism of claim 12, a housing and an assembly platform, an activation mechanism, an insertion mechanism, a fluid pathway connection, a power and control system, and the drive mechanism being mounted on said assembly platform, a contact connected, mounted, printed, or otherwise attached to the ring which, during operation of the drive mechanism, may engage with or disengage from corresponding status switch interconnect to permit a signal from the power and control system to provide feedback to the user.

17. The drug delivery pump of claim 16, wherein the contact may engage with corresponding status switch interconnect to complete a transmission to the power and control system to provide feedback to the user.

18. The drug delivery pump of claim 17, wherein the status switch interconnect is an electrical status switch interconnect and the contact is an electrical contact.

19. The drug delivery pump of claim 16, wherein the contact may disengage from corresponding status switch interconnect to enable transmission of a signal from the power and control system to provide feedback to the user.

20. The drug delivery pump of claim 19, wherein the status switch interconnect is a mechanical trigger member and the contact is a contact pin.

* * * * *